United States Patent
Itagaki et al.

(10) Patent No.: US 6,573,243 B1
(45) Date of Patent: Jun. 3, 2003

(54) POMPILID WASP-DERIVED NEUROPEPTIDES

(75) Inventors: Yasuhiro Itagaki, Fussa (JP); Katsuhiro Konno, Kanagawa (JP); Nobufumi Kawai, Komae (JP); Hiroaki Takayama, Tokyo (JP)

(73) Assignee: Suntory Limited, Osaka (JP)

(*) Notice: Subject to any disclaimer, the term of this patent is extended or adjusted under 35 U.S.C. 154(b) by 0 days.

(21) Appl. No.: 09/486,283

(22) PCT Filed: Aug. 24, 1998

(86) PCT No.: PCT/JP98/03730

§ 371 (c)(1),
(2), (4) Date: May 19, 2000

(87) PCT Pub. No.: WO99/10378

PCT Pub. Date: Mar. 4, 1999

(30) Foreign Application Priority Data

Aug. 25, 1997 (JP) .............................................. 9-241699

(51) Int. Cl.[7] ....................... A61K 38/04; C07K 14/435
(52) U.S. Cl. ............................... 514/14; 514/2; 514/15; 530/300; 530/327; 530/328; 530/412
(58) Field of Search ............................... 514/14, 15, 2; 530/327, 328, 412, 300

(56) References Cited

PUBLICATIONS

Amira Eldefrawi et al., "Structure and Synthesis of a Potent Glutamate Receptor Antagonist in Wasp Venon", *Proc. Nat'l Acad. Sci. USA*, Jul. 1988, vol. 85, pp. 4910–4913.

Katsuhiro Konno et al., " —Pompilidotoxin ( —PMTX), a Novel Neurotoxin from the Venom of a Solidary Wasp, Facilitates Transmission in the Crustracean Neuromuscular Synapse", *Neuroscience Letters*, 1997, pp. 99–102.

Katsuhiro Konno et al., "Isolation and Structure of Pompilidotoxins, Novel Peptide Neurotoxins in Solitary Wasp Venoms", *Biochemical and Biophysical Research Communications*, 1998, pp. 612–616.

*Primary Examiner*—Christopher S. F. Low
*Assistant Examiner*—Chih-Mim Kam
(74) *Attorney, Agent, or Firm*—Crowell & Moring LLP

(57) ABSTRACT

The present invention provides a peptide represented by the amino acid sequence formula (A):

$$\text{H-}X_1\text{-}X_2\text{-}X_3\text{-}X_4\text{-Gly-}X_6\text{-}X_7\text{-Asp-Gln-R} \qquad (A)$$

wherein:
each of $X_1$ and $X_3$ independently represents Arg or Lys, each of $X_2$, $X_4$ and $X_6$ independently represents Ile or Leu, and $X_7$ represents Phe, Tyr or Trp; and R represents -NH$_2$, -Leu-NH$_2$, -Leu-Ser-NH$_2$, -Leu-Ser-Lys-NH$_2$, -Leu-Ser-Arg-NH$_2$, -Leu-Ser-Lys-Leu-NH$_2$, or -Leu-Ser-Arg-Leu-NH$_2$;

and a salt thereof.

(In the above, Gly stands for a glycine residue, Asp stands for an aspartic acid residue, Gln stands for a glutamine residue, Arg stands for an arginine residue, Lys stands for a lysine residue, Ile stands for an isoleucine residue, Leu stands for a leucine residue, Phe stands for a phenylalanine residue, Tyr stands for a tyrosine residue, Trp stands for a tryptophan residue, and Ser stands for a serine residue.)

The peptide acts on glutamate receptors and is expected to be useful in the treatment of cerebral nerve diseases associated with glutamic acid.

6 Claims, No Drawings

SEQUENCE LISTING

<160> NUMBER OF SEQ ID NOS: 203

<210> SEQ ID NO 1

```
<211> LENGTH: 13
<212> TYPE: PRT
<213> ORGANISM: Anoplius samariensis

<400> SEQUENCE: 1

Arg Ile Lys Ile Gly Leu Phe Asp Gln Leu Ser Lys Leu
1               5                   10

<210> SEQ ID NO 2
<211> LENGTH: 13
<212> TYPE: PRT
<213> ORGANISM: Batozonellus maculifrons

<400> SEQUENCE: 2

Arg Ile Lys Ile Gly Leu Phe Asp Gln Leu Ser Arg Leu
1               5                   10

<210> SEQ ID NO 3
<211> LENGTH: 4
<212> TYPE: PRT
<213> ORGANISM: Pompilid sp.

<400> SEQUENCE: 3

Leu Ser Lys Leu
1

<210> SEQ ID NO 4
<211> LENGTH: 4
<212> TYPE: PRT
<213> ORGANISM: Pompilid sp.

<400> SEQUENCE: 4

Leu Ser Arg Leu
1

<210> SEQ ID NO 5
<211> LENGTH: 12
<212> TYPE: PRT
<213> ORGANISM: Pompilid sp.
<220> FEATURE:
<221> NAME/KEY: MISC_FEATURE
<222> LOCATION: (1)..(1)
<223> OTHER INFORMATION: Arg or Lys
<221> NAME/KEY: MISC_FEATURE
<222> LOCATION: (2)..(2)
<223> OTHER INFORMATION: Ile or Leu
<221> NAME/KEY: MISC_FEATURE
<222> LOCATION: (3)..(3)
<223> OTHER INFORMATION: Arg or Lys
<221> NAME/KEY: MISC_FEATURE
<222> LOCATION: (4)..(4)
<223> OTHER INFORMATION: Ile or Leu
<221> NAME/KEY: MISC_FEATURE
<222> LOCATION: (6)..(6)
<223> OTHER INFORMATION: Ile or Leu
<221> NAME/KEY: MISC_FEATURE
<222> LOCATION: (7)..(7)
<223> OTHER INFORMATION: Phe, Tyr or Trp

<400> SEQUENCE: 5

Xaa Xaa Xaa Xaa Gly Xaa Xaa Asp Gln Leu Ser Lys
1               5                   10

<210> SEQ ID NO 6
<211> LENGTH: 12
<212> TYPE: PRT
<213> ORGANISM: Pompilid sp.
<220> FEATURE:
<221> NAME/KEY: MISC_FEATURE
```

```
<222> LOCATION: (1)..(1)
<223> OTHER INFORMATION: Arg or Lys
<221> NAME/KEY: MISC_FEATURE
<222> LOCATION: (2)..(2)
<223> OTHER INFORMATION: Ile or Leu
<221> NAME/KEY: MISC_FEATURE
<222> LOCATION: (3)..(3)
<223> OTHER INFORMATION: Arg or Lys
<221> NAME/KEY: MISC_FEATURE
<222> LOCATION: (4)..(4)
<223> OTHER INFORMATION: Ile or Leu
<221> NAME/KEY: MISC_FEATURE
<222> LOCATION: (6)..(6)
<223> OTHER INFORMATION: Ile or Leu
<221> NAME/KEY: MISC_FEATURE
<222> LOCATION: (7)..(7)
<223> OTHER INFORMATION: Phe, Tyr or Trp

<400> SEQUENCE: 6

Xaa Xaa Xaa Xaa Gly Xaa Xaa Asp Gln Leu Ser Arg
 1               5                  10

<210> SEQ ID NO 7
<211> LENGTH: 13
<212> TYPE: PRT
<213> ORGANISM: Pompilid sp.
<220> FEATURE:
<221> NAME/KEY: MISC_FEATURE
<222> LOCATION: (1)..(1)
<223> OTHER INFORMATION: Arg or Lys
<221> NAME/KEY: MISC_FEATURE
<222> LOCATION: (2)..(2)
<223> OTHER INFORMATION: Ile or Leu
<221> NAME/KEY: MISC_FEATURE
<222> LOCATION: (3)..(3)
<223> OTHER INFORMATION: Arg or Lys
<221> NAME/KEY: MISC_FEATURE
<222> LOCATION: (4)..(4)
<223> OTHER INFORMATION: Ile or Leu
<221> NAME/KEY: MISC_FEATURE
<222> LOCATION: (6)..(6)
<223> OTHER INFORMATION: Ile or Leu
<221> NAME/KEY: MISC_FEATURE
<222> LOCATION: (7)..(7)
<223> OTHER INFORMATION: Phe, Tyr or Trp

<400> SEQUENCE: 7

Xaa Xaa Xaa Xaa Gly Xaa Xaa Asp Gln Leu Ser Lys Leu
 1               5                  10

<210> SEQ ID NO 8
<211> LENGTH: 13
<212> TYPE: PRT
<213> ORGANISM: Pompilid sp.
<220> FEATURE:
<221> NAME/KEY: MISC_FEATURE
<222> LOCATION: (1)..(1)
<223> OTHER INFORMATION: Arg or Lys
<221> NAME/KEY: MISC_FEATURE
<222> LOCATION: (2)..(2)
<223> OTHER INFORMATION: Ile or Leu
<221> NAME/KEY: MISC_FEATURE
<222> LOCATION: (3)..(3)
<223> OTHER INFORMATION: Arg or Lys
<221> NAME/KEY: MISC_FEATURE
<222> LOCATION: (4)..(4)
<223> OTHER INFORMATION: Ile or Leu
<221> NAME/KEY: MISC_FEATURE
<222> LOCATION: (6)..(6)
<223> OTHER INFORMATION: Ile or Leu
<221> NAME/KEY: MISC_FEATURE
<222> LOCATION: (7)..(7)
<223> OTHER INFORMATION: Phe, Tyr or Trp

<400> SEQUENCE: 8
```

Xaa Xaa Xaa Xaa Gly Xaa Xaa Asp Gln Leu Ser Arg Leu
1               5                   10

<210> SEQ ID NO 9
<211> LENGTH: 13
<212> TYPE: PRT
<213> ORGANISM: Pompilid sp.

<400> SEQUENCE: 9

Arg Ile Lys Ile Gly Leu Tyr Asp Gln Leu Ser Lys Leu
1               5                   10

<210> SEQ ID NO 10
<211> LENGTH: 13
<212> TYPE: PRT
<213> ORGANISM: Pompilid sp.

<400> SEQUENCE: 10

Arg Ile Lys Ile Gly Leu Trp Asp Gln Leu Ser Lys Leu
1               5                   10

<210> SEQ ID NO 11
<211> LENGTH: 13
<212> TYPE: PRT
<213> ORGANISM: Pompilid sp.

<400> SEQUENCE: 11

Arg Ile Lys Ile Gly Ile Phe Asp Gln Leu Ser Lys Leu
1               5                   10

<210> SEQ ID NO 12
<211> LENGTH: 13
<212> TYPE: PRT
<213> ORGANISM: Pompilid sp.

<400> SEQUENCE: 12

Arg Ile Lys Ile Gly Ile Tyr Asp Gln Leu Ser Lys Leu
1               5                   10

<210> SEQ ID NO 13
<211> LENGTH: 13
<212> TYPE: PRT
<213> ORGANISM: Pompilid sp.

<400> SEQUENCE: 13

Arg Ile Lys Ile Gly Ile Trp Asp Gln Leu Ser Lys Leu
1               5                   10

<210> SEQ ID NO 14
<211> LENGTH: 13
<212> TYPE: PRT
<213> ORGANISM: Pompilid sp.

<400> SEQUENCE: 14

Arg Ile Lys Leu Gly Leu Phe Asp Gln Leu Ser Lys Leu
1               5                   10

<210> SEQ ID NO 15
<211> LENGTH: 13
<212> TYPE: PRT
<213> ORGANISM: Pompilid sp.

<400> SEQUENCE: 15

Arg Ile Lys Leu Gly Leu Tyr Asp Gln Leu Ser Lys Leu

-continued

```
1               5               10
```

<210> SEQ ID NO 16
<211> LENGTH: 13
<212> TYPE: PRT
<213> ORGANISM: Pompilid sp.

<400> SEQUENCE: 16

```
Arg Ile Lys Leu Gly Leu Trp Asp Gln Leu Ser Lys Leu
1               5                  10
```

<210> SEQ ID NO 17
<211> LENGTH: 13
<212> TYPE: PRT
<213> ORGANISM: Pompilid sp.

<400> SEQUENCE: 17

```
Arg Ile Lys Leu Gly Ile Phe Asp Gln Leu Ser Lys Leu
1               5                  10
```

<210> SEQ ID NO 18
<211> LENGTH: 13
<212> TYPE: PRT
<213> ORGANISM: Pompilid sp.

<400> SEQUENCE: 18

```
Arg Ile Lys Leu Gly Ile Tyr Asp Gln Leu Ser Lys Leu
1               5                  10
```

<210> SEQ ID NO 19
<211> LENGTH: 13
<212> TYPE: PRT
<213> ORGANISM: Pompilid sp.

<400> SEQUENCE: 19

```
Arg Ile Lys Leu Gly Ile Trp Asp Gln Leu Ser Lys Leu
1               5                  10
```

<210> SEQ ID NO 20
<211> LENGTH: 13
<212> TYPE: PRT
<213> ORGANISM: Pompilid sp.

<400> SEQUENCE: 20

```
Arg Ile Arg Ile Gly Leu Phe Asp Gln Leu Ser Lys Leu
1               5                  10
```

<210> SEQ ID NO 21
<211> LENGTH: 13
<212> TYPE: PRT
<213> ORGANISM: Pompilid sp.

<400> SEQUENCE: 21

```
Arg Ile Arg Ile Gly Leu Tyr Asp Gln Leu Ser Lys Leu
1               5                  10
```

<210> SEQ ID NO 22
<211> LENGTH: 13
<212> TYPE: PRT
<213> ORGANISM: Pompilid sp.

<400> SEQUENCE: 22

```
Arg Ile Arg Ile Gly Leu Trp Asp Gln Leu Ser Lys Leu
1               5                  10
```

<210> SEQ ID NO 23
<211> LENGTH: 13
<212> TYPE: PRT
<213> ORGANISM: Pompilid sp.

<400> SEQUENCE: 23

Arg Ile Arg Ile Gly Ile Phe Asp Gln Leu Ser Lys Leu
1               5                   10

<210> SEQ ID NO 24
<211> LENGTH: 13
<212> TYPE: PRT
<213> ORGANISM: Pompilid sp.

<400> SEQUENCE: 24

Arg Ile Arg Ile Gly Ile Tyr Asp Gln Leu Ser Lys Leu
1               5                   10

<210> SEQ ID NO 25
<211> LENGTH: 13
<212> TYPE: PRT
<213> ORGANISM: Pompilid sp.

<400> SEQUENCE: 25

Arg Ile Arg Ile Gly Ile Trp Asp Gln Leu Ser Lys Leu
1               5                   10

<210> SEQ ID NO 26
<211> LENGTH: 13
<212> TYPE: PRT
<213> ORGANISM: Pompilid sp.

<400> SEQUENCE: 26

Arg Ile Arg Leu Gly Leu Phe Asp Gln Leu Ser Lys Leu
1               5                   10

<210> SEQ ID NO 27
<211> LENGTH: 13
<212> TYPE: PRT
<213> ORGANISM: Pompilid sp.

<400> SEQUENCE: 27

Arg Ile Arg Leu Gly Leu Tyr Asp Gln Leu Ser Lys Leu
1               5                   10

<210> SEQ ID NO 28
<211> LENGTH: 13
<212> TYPE: PRT
<213> ORGANISM: Pompilid sp.

<400> SEQUENCE: 28

Arg Ile Arg Leu Gly Leu Trp Asp Gln Leu Ser Lys Leu
1               5                   10

<210> SEQ ID NO 29
<211> LENGTH: 13
<212> TYPE: PRT
<213> ORGANISM: Pompilid sp.

<400> SEQUENCE: 29

Arg Ile Arg Leu Gly Ile Phe Asp Gln Leu Ser Lys Leu
1               5                   10

<210> SEQ ID NO 30

```
<211> LENGTH: 13
<212> TYPE: PRT
<213> ORGANISM: Pompilid sp.

<400> SEQUENCE: 30

Arg Ile Arg Leu Gly Ile Tyr Asp Gln Leu Ser Lys Leu
1               5                   10

<210> SEQ ID NO 31
<211> LENGTH: 13
<212> TYPE: PRT
<213> ORGANISM: Pompilid sp.

<400> SEQUENCE: 31

Arg Ile Arg Leu Gly Ile Trp Asp Gln Leu Ser Lys Leu
1               5                   10

<210> SEQ ID NO 32
<211> LENGTH: 13
<212> TYPE: PRT
<213> ORGANISM: Pompilid sp.

<400> SEQUENCE: 32

Arg Leu Lys Ile Gly Leu Phe Asp Gln Leu Ser Lys Leu
1               5                   10

<210> SEQ ID NO 33
<211> LENGTH: 13
<212> TYPE: PRT
<213> ORGANISM: Pompilid sp.

<400> SEQUENCE: 33

Arg Leu Lys Ile Gly Leu Tyr Asp Gln Leu Ser Lys Leu
1               5                   10

<210> SEQ ID NO 34
<211> LENGTH: 13
<212> TYPE: PRT
<213> ORGANISM: Pompilid sp.

<400> SEQUENCE: 34

Arg Leu Lys Ile Gly Leu Trp Asp Gln Leu Ser Lys Leu
1               5                   10

<210> SEQ ID NO 35
<211> LENGTH: 13
<212> TYPE: PRT
<213> ORGANISM: Pompilid sp.

<400> SEQUENCE: 35

Arg Leu Lys Ile Gly Ile Phe Asp Gln Leu Ser Lys Leu
1               5                   10

<210> SEQ ID NO 36
<211> LENGTH: 13
<212> TYPE: PRT
<213> ORGANISM: Pompilid sp.

<400> SEQUENCE: 36

Arg Leu Lys Ile Gly Ile Tyr Asp Gln Leu Ser Lys Leu
1               5                   10

<210> SEQ ID NO 37
<211> LENGTH: 13
<212> TYPE: PRT
```

<213> ORGANISM: Pompilid sp.

<400> SEQUENCE: 37

Arg Leu Lys Ile Gly Ile Trp Asp Gln Leu Ser Lys Leu
1               5                   10

<210> SEQ ID NO 38
<211> LENGTH: 13
<212> TYPE: PRT
<213> ORGANISM: Pompilid sp.

<400> SEQUENCE: 38

Arg Leu Lys Leu Gly Leu Phe Asp Gln Leu Ser Lys Leu
1               5                   10

<210> SEQ ID NO 39
<211> LENGTH: 13
<212> TYPE: PRT
<213> ORGANISM: Pompilid sp.

<400> SEQUENCE: 39

Arg Leu Lys Leu Gly Leu Tyr Asp Gln Leu Ser Lys Leu
1               5                   10

<210> SEQ ID NO 40
<211> LENGTH: 13
<212> TYPE: PRT
<213> ORGANISM: Pompilid sp.

<400> SEQUENCE: 40

Arg Leu Lys Leu Gly Leu Trp Asp Gln Leu Ser Lys Leu
1               5                   10

<210> SEQ ID NO 41
<211> LENGTH: 13
<212> TYPE: PRT
<213> ORGANISM: Pompilid sp.

<400> SEQUENCE: 41

Arg Leu Lys Leu Gly Ile Phe Asp Gln Leu Ser Lys Leu
1               5                   10

<210> SEQ ID NO 42
<211> LENGTH: 13
<212> TYPE: PRT
<213> ORGANISM: Pompilid sp.

<400> SEQUENCE: 42

Arg Leu Lys Leu Gly Ile Tyr Asp Gln Leu Ser Lys Leu
1               5                   10

<210> SEQ ID NO 43
<211> LENGTH: 13
<212> TYPE: PRT
<213> ORGANISM: Pompilid sp.

<400> SEQUENCE: 43

Arg Leu Lys Leu Gly Ile Trp Asp Gln Leu Ser Lys Leu
1               5                   10

<210> SEQ ID NO 44
<211> LENGTH: 13
<212> TYPE: PRT
<213> ORGANISM: Pompilid sp.

```
<400> SEQUENCE: 44

Arg Leu Arg Ile Gly Leu Phe Asp Gln Leu Ser Lys Leu
1               5                   10

<210> SEQ ID NO 45
<211> LENGTH: 13
<212> TYPE: PRT
<213> ORGANISM: Pompilid sp.

<400> SEQUENCE: 45

Arg Leu Arg Ile Gly Leu Tyr Asp Gln Leu Ser Lys Leu
1               5                   10

<210> SEQ ID NO 46
<211> LENGTH: 13
<212> TYPE: PRT
<213> ORGANISM: Pompilid sp.

<400> SEQUENCE: 46

Arg Leu Arg Ile Gly Leu Trp Asp Gln Leu Ser Lys Leu
1               5                   10

<210> SEQ ID NO 47
<211> LENGTH: 13
<212> TYPE: PRT
<213> ORGANISM: Pompilid sp.

<400> SEQUENCE: 47

Arg Leu Arg Ile Gly Ile Phe Asp Gln Leu Ser Lys Leu
1               5                   10

<210> SEQ ID NO 48
<211> LENGTH: 13
<212> TYPE: PRT
<213> ORGANISM: Pompilid sp.

<400> SEQUENCE: 48

Arg Leu Arg Ile Gly Ile Tyr Asp Gln Leu Ser Lys Leu
1               5                   10

<210> SEQ ID NO 49
<211> LENGTH: 13
<212> TYPE: PRT
<213> ORGANISM: Pompilid sp.

<400> SEQUENCE: 49

Arg Leu Arg Ile Gly Ile Trp Asp Gln Leu Ser Lys Leu
1               5                   10

<210> SEQ ID NO 50
<211> LENGTH: 13
<212> TYPE: PRT
<213> ORGANISM: Pompilid sp.

<400> SEQUENCE: 50

Arg Leu Arg Leu Gly Leu Phe Asp Gln Leu Ser Lys Leu
1               5                   10

<210> SEQ ID NO 51
<211> LENGTH: 13
<212> TYPE: PRT
<213> ORGANISM: Pompilid sp.

<400> SEQUENCE: 51
```

-continued

Arg Leu Arg Leu Gly Leu Tyr Asp Gln Leu Ser Lys Leu
1               5                   10

<210> SEQ ID NO 52
<211> LENGTH: 13
<212> TYPE: PRT
<213> ORGANISM: Pompilid sp.

<400> SEQUENCE: 52

Arg Leu Arg Leu Gly Leu Trp Asp Gln Leu Ser Lys Leu
1               5                   10

<210> SEQ ID NO 53
<211> LENGTH: 13
<212> TYPE: PRT
<213> ORGANISM: Pompilid sp.

<400> SEQUENCE: 53

Arg Leu Arg Leu Gly Ile Phe Asp Gln Leu Ser Lys Leu
1               5                   10

<210> SEQ ID NO 54
<211> LENGTH: 13
<212> TYPE: PRT
<213> ORGANISM: Pompilid sp.

<400> SEQUENCE: 54

Arg Leu Arg Leu Gly Ile Tyr Asp Gln Leu Ser Lys Leu
1               5                   10

<210> SEQ ID NO 55
<211> LENGTH: 13
<212> TYPE: PRT
<213> ORGANISM: Pompilid sp.

<400> SEQUENCE: 55

Arg Leu Arg Leu Gly Ile Trp Asp Gln Leu Ser Lys Leu
1               5                   10

<210> SEQ ID NO 56
<211> LENGTH: 13
<212> TYPE: PRT
<213> ORGANISM: Pompilid sp.

<400> SEQUENCE: 56

Lys Ile Lys Ile Gly Leu Phe Asp Gln Leu Ser Lys Leu
1               5                   10

<210> SEQ ID NO 57
<211> LENGTH: 13
<212> TYPE: PRT
<213> ORGANISM: Pompilid sp.

<400> SEQUENCE: 57

Lys Ile Lys Ile Gly Leu Tyr Asp Gln Leu Ser Lys Leu
1               5                   10

<210> SEQ ID NO 58
<211> LENGTH: 13
<212> TYPE: PRT
<213> ORGANISM: Pompilid sp.

<400> SEQUENCE: 58

Lys Ile Lys Ile Gly Leu Trp Asp Gln Leu Ser Lys Leu
1               5                   10

<210> SEQ ID NO 59
<211> LENGTH: 13
<212> TYPE: PRT
<213> ORGANISM: Pompilid sp.

<400> SEQUENCE: 59

Lys Ile Lys Ile Gly Ile Phe Asp Gln Leu Ser Lys Leu
1               5                   10

<210> SEQ ID NO 60
<211> LENGTH: 13
<212> TYPE: PRT
<213> ORGANISM: Pompilid sp.

<400> SEQUENCE: 60

Lys Ile Lys Ile Gly Ile Tyr Asp Gln Leu Ser Lys Leu
1               5                   10

<210> SEQ ID NO 61
<211> LENGTH: 13
<212> TYPE: PRT
<213> ORGANISM: Pompilid sp.

<400> SEQUENCE: 61

Lys Ile Lys Ile Gly Ile Trp Asp Gln Leu Ser Lys Leu
1               5                   10

<210> SEQ ID NO 62
<211> LENGTH: 13
<212> TYPE: PRT
<213> ORGANISM: Pompilid sp.

<400> SEQUENCE: 62

Lys Ile Lys Leu Gly Leu Phe Asp Gln Leu Ser Lys Leu
1               5                   10

<210> SEQ ID NO 63
<211> LENGTH: 13
<212> TYPE: PRT
<213> ORGANISM: Pompilid sp.

<400> SEQUENCE: 63

Lys Ile Lys Leu Gly Leu Tyr Asp Gln Leu Ser Lys Leu
1               5                   10

<210> SEQ ID NO 64
<211> LENGTH: 13
<212> TYPE: PRT
<213> ORGANISM: Pompilid sp.

<400> SEQUENCE: 64

Lys Ile Lys Leu Gly Leu Trp Asp Gln Leu Ser Lys Leu
1               5                   10

<210> SEQ ID NO 65
<211> LENGTH: 13
<212> TYPE: PRT
<213> ORGANISM: Pompilid sp.

<400> SEQUENCE: 65

Lys Ile Lys Leu Gly Ile Phe Asp Gln Leu Ser Lys Leu
1               5                   10

<210> SEQ ID NO 66
<211> LENGTH: 13
<212> TYPE: PRT
<213> ORGANISM: Pompilid sp.

<400> SEQUENCE: 66

Lys Ile Lys Leu Gly Ile Tyr Asp Gln Leu Ser Lys Leu
1               5                   10

<210> SEQ ID NO 67
<211> LENGTH: 13
<212> TYPE: PRT
<213> ORGANISM: Pompilid sp.

<400> SEQUENCE: 67

Lys Ile Lys Leu Gly Ile Trp Asp Gln Leu Ser Lys Leu
1               5                   10

<210> SEQ ID NO 68
<211> LENGTH: 13
<212> TYPE: PRT
<213> ORGANISM: Pompilid sp.

<400> SEQUENCE: 68

Lys Ile Arg Ile Gly Leu Phe Asp Gln Leu Ser Lys Leu
1               5                   10

<210> SEQ ID NO 69
<211> LENGTH: 13
<212> TYPE: PRT
<213> ORGANISM: Pompilid sp.

<400> SEQUENCE: 69

Lys Ile Arg Ile Gly Leu Tyr Asp Gln Leu Ser Lys Leu
1               5                   10

<210> SEQ ID NO 70
<211> LENGTH: 13
<212> TYPE: PRT
<213> ORGANISM: Pompilid sp.

<400> SEQUENCE: 70

Lys Ile Arg Ile Gly Leu Trp Asp Gln Leu Ser Lys Leu
1               5                   10

<210> SEQ ID NO 71
<211> LENGTH: 13
<212> TYPE: PRT
<213> ORGANISM: Pompilid sp.

<400> SEQUENCE: 71

Lys Ile Arg Ile Gly Ile Phe Asp Gln Leu Ser Lys Leu
1               5                   10

<210> SEQ ID NO 72
<211> LENGTH: 13
<212> TYPE: PRT
<213> ORGANISM: Pompilid sp.

<400> SEQUENCE: 72

Lys Ile Arg Ile Gly Ile Tyr Asp Gln Leu Ser Lys Leu
1               5                   10

<210> SEQ ID NO 73
<211> LENGTH: 13

```
<212> TYPE: PRT
<213> ORGANISM: Pompilid sp.

<400> SEQUENCE: 73

Lys Ile Arg Ile Gly Ile Trp Asp Gln Leu Ser Lys Leu
1               5                   10

<210> SEQ ID NO 74
<211> LENGTH: 13
<212> TYPE: PRT
<213> ORGANISM: Pompilid sp.

<400> SEQUENCE: 74

Lys Ile Arg Leu Gly Leu Phe Asp Gln Leu Ser Lys Leu
1               5                   10

<210> SEQ ID NO 75
<211> LENGTH: 12
<212> TYPE: PRT
<213> ORGANISM: Pompilid sp.

<400> SEQUENCE: 75

Lys Ile Arg Leu Gly Tyr Asp Gln Leu Ser Lys Leu
1               5                   10

<210> SEQ ID NO 76
<211> LENGTH: 13
<212> TYPE: PRT
<213> ORGANISM: Pompilid sp.

<400> SEQUENCE: 76

Lys Ile Arg Leu Gly Leu Trp Asp Gln Leu Ser Lys Leu
1               5                   10

<210> SEQ ID NO 77
<211> LENGTH: 13
<212> TYPE: PRT
<213> ORGANISM: Pompilid sp.

<400> SEQUENCE: 77

Lys Ile Arg Leu Gly Ile Phe Asp Gln Leu Ser Lys Leu
1               5                   10

<210> SEQ ID NO 78
<211> LENGTH: 13
<212> TYPE: PRT
<213> ORGANISM: Pompilid sp.

<400> SEQUENCE: 78

Lys Ile Arg Leu Gly Ile Tyr Asp Gln Leu Ser Lys Leu
1               5                   10

<210> SEQ ID NO 79
<211> LENGTH: 13
<212> TYPE: PRT
<213> ORGANISM: Pompilid sp.

<400> SEQUENCE: 79

Lys Ile Arg Leu Gly Ile Trp Asp Gln Leu Ser Lys Leu
1               5                   10

<210> SEQ ID NO 80
<211> LENGTH: 13
<212> TYPE: PRT
<213> ORGANISM: Pompilid sp.
```

<400> SEQUENCE: 80

Lys Leu Lys Ile Gly Leu Phe Asp Gln Leu Ser Lys Leu
1               5                   10

<210> SEQ ID NO 81
<211> LENGTH: 13
<212> TYPE: PRT
<213> ORGANISM: Pompilid sp.

<400> SEQUENCE: 81

Lys Leu Lys Ile Gly Leu Tyr Asp Gln Leu Ser Lys Leu
1               5                   10

<210> SEQ ID NO 82
<211> LENGTH: 13
<212> TYPE: PRT
<213> ORGANISM: Pompilid sp.

<400> SEQUENCE: 82

Lys Leu Lys Ile Gly Leu Trp Asp Gln Leu Ser Lys Leu
1               5                   10

<210> SEQ ID NO 83
<211> LENGTH: 13
<212> TYPE: PRT
<213> ORGANISM: Pompilid sp.

<400> SEQUENCE: 83

Lys Leu Lys Ile Gly Ile Phe Asp Gln Leu Ser Lys Leu
1               5                   10

<210> SEQ ID NO 84
<211> LENGTH: 13
<212> TYPE: PRT
<213> ORGANISM: Pompilid sp.

<400> SEQUENCE: 84

Lys Leu Lys Ile Gly Ile Tyr Asp Gln Leu Ser Lys Leu
1               5                   10

<210> SEQ ID NO 85
<211> LENGTH: 13
<212> TYPE: PRT
<213> ORGANISM: Pompilid sp.

<400> SEQUENCE: 85

Lys Leu Lys Ile Gly Ile Trp Asp Gln Leu Ser Lys Leu
1               5                   10

<210> SEQ ID NO 86
<211> LENGTH: 13
<212> TYPE: PRT
<213> ORGANISM: Pompilid sp.

<400> SEQUENCE: 86

Lys Leu Lys Leu Gly Leu Phe Asp Gln Leu Ser Lys Leu
1               5                   10

<210> SEQ ID NO 87
<211> LENGTH: 13
<212> TYPE: PRT
<213> ORGANISM: Pompilid sp.

<400> SEQUENCE: 87

```
Lys Leu Lys Leu Gly Leu Tyr Asp Gln Leu Ser Lys Leu
1               5                   10
```

<210> SEQ ID NO 88
<211> LENGTH: 13
<212> TYPE: PRT
<213> ORGANISM: Pompilid sp.

<400> SEQUENCE: 88

```
Lys Leu Lys Leu Gly Leu Trp Asp Gln Leu Ser Lys Leu
1               5                   10
```

<210> SEQ ID NO 89
<211> LENGTH: 13
<212> TYPE: PRT
<213> ORGANISM: Pompilid sp.

<400> SEQUENCE: 89

```
Lys Leu Lys Leu Gly Ile Phe Asp Gln Leu Ser Lys Leu
1               5                   10
```

<210> SEQ ID NO 90
<211> LENGTH: 13
<212> TYPE: PRT
<213> ORGANISM: Pompilid sp.

<400> SEQUENCE: 90

```
Lys Leu Lys Leu Gly Ile Tyr Asp Gln Leu Ser Lys Leu
1               5                   10
```

<210> SEQ ID NO 91
<211> LENGTH: 13
<212> TYPE: PRT
<213> ORGANISM: Pompilid sp.

<400> SEQUENCE: 91

```
Lys Leu Lys Leu Gly Ile Trp Asp Gln Leu Ser Lys Leu
1               5                   10
```

<210> SEQ ID NO 92
<211> LENGTH: 13
<212> TYPE: PRT
<213> ORGANISM: Pompilid sp.

<400> SEQUENCE: 92

```
Lys Leu Arg Ile Gly Leu Phe Asp Gln Leu Ser Lys Leu
1               5                   10
```

<210> SEQ ID NO 93
<211> LENGTH: 13
<212> TYPE: PRT
<213> ORGANISM: Pompilid sp.

<400> SEQUENCE: 93

```
Lys Leu Arg Ile Gly Leu Tyr Asp Gln Leu Ser Lys Leu
1               5                   10
```

<210> SEQ ID NO 94
<211> LENGTH: 13
<212> TYPE: PRT
<213> ORGANISM: Pompilid sp.

<400> SEQUENCE: 94

```
Lys Leu Arg Ile Gly Leu Trp Asp Gln Leu Ser Lys Leu
```

-continued

```
1               5                   10
```

<210> SEQ ID NO 95
<211> LENGTH: 13
<212> TYPE: PRT
<213> ORGANISM: Pompilid sp.

<400> SEQUENCE: 95

```
Lys Leu Arg Ile Gly Ile Phe Asp Gln Leu Ser Lys Leu
1               5                   10
```

<210> SEQ ID NO 96
<211> LENGTH: 13
<212> TYPE: PRT
<213> ORGANISM: Pompilid sp.

<400> SEQUENCE: 96

```
Lys Leu Arg Ile Gly Ile Tyr Asp Gln Leu Ser Lys Leu
1               5                   10
```

<210> SEQ ID NO 97
<211> LENGTH: 13
<212> TYPE: PRT
<213> ORGANISM: Pompilid sp.

<400> SEQUENCE: 97

```
Lys Leu Arg Ile Gly Ile Trp Asp Gln Leu Ser Lys Leu
1               5                   10
```

<210> SEQ ID NO 98
<211> LENGTH: 13
<212> TYPE: PRT
<213> ORGANISM: Pompilid sp.

<400> SEQUENCE: 98

```
Lys Leu Arg Leu Gly Leu Phe Asp Gln Leu Ser Lys Leu
1               5                   10
```

<210> SEQ ID NO 99
<211> LENGTH: 13
<212> TYPE: PRT
<213> ORGANISM: Pompilid sp.

<400> SEQUENCE: 99

```
Lys Leu Arg Leu Gly Leu Tyr Asp Gln Leu Ser Lys Leu
1               5                   10
```

<210> SEQ ID NO 100
<211> LENGTH: 13
<212> TYPE: PRT
<213> ORGANISM: Pompilid sp.

<400> SEQUENCE: 100

```
Lys Leu Arg Leu Gly Leu Trp Asp Gln Leu Ser Lys Leu
1               5                   10
```

<210> SEQ ID NO 101
<211> LENGTH: 13
<212> TYPE: PRT
<213> ORGANISM: Pompilid sp.

<400> SEQUENCE: 101

```
Lys Leu Arg Leu Gly Ile Phe Asp Gln Leu Ser Lys Leu
1               5                   10
```

```
<210> SEQ ID NO 102
<211> LENGTH: 13
<212> TYPE: PRT
<213> ORGANISM: Pompilid sp.

<400> SEQUENCE: 102

Lys Leu Arg Leu Gly Ile Tyr Asp Gln Leu Ser Lys Leu
1               5                   10

<210> SEQ ID NO 103
<211> LENGTH: 13
<212> TYPE: PRT
<213> ORGANISM: Pompilid sp.

<400> SEQUENCE: 103

Lys Leu Arg Leu Gly Ile Trp Asp Gln Leu Ser Lys Leu
1               5                   10

<210> SEQ ID NO 104
<211> LENGTH: 13
<212> TYPE: PRT
<213> ORGANISM: Pompilid sp.

<400> SEQUENCE: 104

Arg Ile Lys Ile Gly Leu Tyr Asp Gln Leu Ser Arg Leu
1               5                   10

<210> SEQ ID NO 105
<211> LENGTH: 13
<212> TYPE: PRT
<213> ORGANISM: Pompilid sp.

<400> SEQUENCE: 105

Arg Ile Lys Ile Gly Leu Trp Asp Gln Leu Ser Arg Leu
1               5                   10

<210> SEQ ID NO 106
<211> LENGTH: 13
<212> TYPE: PRT
<213> ORGANISM: Pompilid sp.

<400> SEQUENCE: 106

Arg Ile Lys Ile Gly Ile Phe Asp Gln Leu Ser Arg Leu
1               5                   10

<210> SEQ ID NO 107
<211> LENGTH: 13
<212> TYPE: PRT
<213> ORGANISM: Pompilid sp.

<400> SEQUENCE: 107

Arg Ile Lys Ile Gly Ile Tyr Asp Gln Leu Ser Arg Leu
1               5                   10

<210> SEQ ID NO 108
<211> LENGTH: 13
<212> TYPE: PRT
<213> ORGANISM: Pompilid sp.

<400> SEQUENCE: 108

Arg Ile Lys Ile Gly Ile Trp Asp Gln Leu Ser Arg Leu
1               5                   10

<210> SEQ ID NO 109
```

```
<211> LENGTH: 13
<212> TYPE: PRT
<213> ORGANISM: Pompilid sp.

<400> SEQUENCE: 109

Arg Ile Lys Leu Gly Leu Phe Asp Gln Leu Ser Arg Leu
1               5                   10

<210> SEQ ID NO 110
<211> LENGTH: 13
<212> TYPE: PRT
<213> ORGANISM: Pompilid sp.

<400> SEQUENCE: 110

Arg Ile Lys Leu Gly Leu Tyr Asp Gln Leu Ser Arg Leu
1               5                   10

<210> SEQ ID NO 111
<211> LENGTH: 13
<212> TYPE: PRT
<213> ORGANISM: Pompilid sp.

<400> SEQUENCE: 111

Arg Ile Lys Leu Gly Leu Trp Asp Gln Leu Ser Arg Leu
1               5                   10

<210> SEQ ID NO 112
<211> LENGTH: 13
<212> TYPE: PRT
<213> ORGANISM: Pompilid sp.

<400> SEQUENCE: 112

Arg Ile Lys Leu Gly Ile Phe Asp Gln Leu Ser Arg Leu
1               5                   10

<210> SEQ ID NO 113
<211> LENGTH: 13
<212> TYPE: PRT
<213> ORGANISM: Pompilid sp.

<400> SEQUENCE: 113

Arg Ile Lys Leu Gly Ile Tyr Asp Gln Leu Ser Arg Leu
1               5                   10

<210> SEQ ID NO 114
<211> LENGTH: 13
<212> TYPE: PRT
<213> ORGANISM: Pompilid sp.

<400> SEQUENCE: 114

Arg Ile Lys Leu Gly Ile Trp Asp Gln Leu Ser Arg Leu
1               5                   10

<210> SEQ ID NO 115
<211> LENGTH: 13
<212> TYPE: PRT
<213> ORGANISM: Pompilid sp.

<400> SEQUENCE: 115

Arg Ile Arg Ile Gly Leu Phe Asp Gln Leu Ser Arg Leu
1               5                   10

<210> SEQ ID NO 116
<211> LENGTH: 13
<212> TYPE: PRT
```

<213> ORGANISM: Pompilid sp.

<400> SEQUENCE: 116

Arg Ile Arg Ile Gly Leu Tyr Asp Gln Leu Ser Arg Leu
1               5                   10

<210> SEQ ID NO 117
<211> LENGTH: 13
<212> TYPE: PRT
<213> ORGANISM: Pompilid sp.

<400> SEQUENCE: 117

Arg Ile Arg Ile Gly Leu Trp Asp Gln Leu Ser Arg Leu
1               5                   10

<210> SEQ ID NO 118
<211> LENGTH: 13
<212> TYPE: PRT
<213> ORGANISM: Pompilid sp.

<400> SEQUENCE: 118

Arg Ile Arg Ile Gly Ile Phe Asp Gln Leu Ser Arg Leu
1               5                   10

<210> SEQ ID NO 119
<211> LENGTH: 13
<212> TYPE: PRT
<213> ORGANISM: Pompilid sp.

<400> SEQUENCE: 119

Arg Ile Arg Ile Gly Ile Tyr Asp Gln Leu Ser Arg Leu
1               5                   10

<210> SEQ ID NO 120
<211> LENGTH: 13
<212> TYPE: PRT
<213> ORGANISM: Pompilid sp.

<400> SEQUENCE: 120

Arg Ile Arg Ile Gly Ile Trp Asp Gln Leu Ser Arg Leu
1               5                   10

<210> SEQ ID NO 121
<211> LENGTH: 13
<212> TYPE: PRT
<213> ORGANISM: Pompilid sp.

<400> SEQUENCE: 121

Arg Ile Arg Leu Gly Leu Phe Asp Gln Leu Ser Arg Leu
1               5                   10

<210> SEQ ID NO 122
<211> LENGTH: 13
<212> TYPE: PRT
<213> ORGANISM: Pompilid sp.

<400> SEQUENCE: 122

Arg Ile Arg Leu Gly Leu Tyr Asp Gln Leu Ser Arg Leu
1               5                   10

<210> SEQ ID NO 123
<211> LENGTH: 13
<212> TYPE: PRT
<213> ORGANISM: Pompilid sp.

```
<400> SEQUENCE: 123

Arg Ile Arg Leu Gly Leu Trp Asp Gln Leu Ser Arg Leu
1               5                   10

<210> SEQ ID NO 124
<211> LENGTH: 13
<212> TYPE: PRT
<213> ORGANISM: Pompilid sp.

<400> SEQUENCE: 124

Arg Ile Arg Leu Gly Ile Phe Asp Gln Leu Ser Arg Leu
1               5                   10

<210> SEQ ID NO 125
<211> LENGTH: 13
<212> TYPE: PRT
<213> ORGANISM: Pompilid sp.

<400> SEQUENCE: 125

Arg Ile Arg Leu Gly Ile Tyr Asp Gln Leu Ser Arg Leu
1               5                   10

<210> SEQ ID NO 126
<211> LENGTH: 13
<212> TYPE: PRT
<213> ORGANISM: Pompilid sp.

<400> SEQUENCE: 126

Arg Ile Arg Leu Gly Ile Trp Asp Gln Leu Ser Arg Leu
1               5                   10

<210> SEQ ID NO 127
<211> LENGTH: 13
<212> TYPE: PRT
<213> ORGANISM: Pompilid sp.

<400> SEQUENCE: 127

Arg Leu Lys Ile Gly Leu Phe Asp Gln Leu Ser Arg Leu
1               5                   10

<210> SEQ ID NO 128
<211> LENGTH: 13
<212> TYPE: PRT
<213> ORGANISM: Pompilid sp.

<400> SEQUENCE: 128

Arg Leu Lys Ile Gly Leu Tyr Asp Gln Leu Ser Arg Leu
1               5                   10

<210> SEQ ID NO 129
<211> LENGTH: 13
<212> TYPE: PRT
<213> ORGANISM: Pompilid sp.

<400> SEQUENCE: 129

Arg Leu Lys Ile Gly Leu Trp Asp Gln Leu Ser Arg Leu
1               5                   10

<210> SEQ ID NO 130
<211> LENGTH: 13
<212> TYPE: PRT
<213> ORGANISM: Pompilid sp.

<400> SEQUENCE: 130
```

Arg Leu Lys Ile Gly Ile Phe Asp Gln Leu Ser Arg Leu
1               5                   10

<210> SEQ ID NO 131
<211> LENGTH: 13
<212> TYPE: PRT
<213> ORGANISM: Pompilid sp.

<400> SEQUENCE: 131

Arg Leu Lys Ile Gly Ile Tyr Asp Gln Leu Ser Arg Leu
1               5                   10

<210> SEQ ID NO 132
<211> LENGTH: 13
<212> TYPE: PRT
<213> ORGANISM: Pompilid sp.

<400> SEQUENCE: 132

Arg Leu Lys Ile Gly Ile Trp Asp Gln Leu Ser Arg Leu
1               5                   10

<210> SEQ ID NO 133
<211> LENGTH: 13
<212> TYPE: PRT
<213> ORGANISM: Pompilid sp.

<400> SEQUENCE: 133

Arg Leu Lys Leu Gly Leu Phe Asp Gln Leu Ser Arg Leu
1               5                   10

<210> SEQ ID NO 134
<211> LENGTH: 13
<212> TYPE: PRT
<213> ORGANISM: Pompilid sp.

<400> SEQUENCE: 134

Arg Leu Lys Leu Gly Leu Tyr Asp Gln Leu Ser Arg Leu
1               5                   10

<210> SEQ ID NO 135
<211> LENGTH: 13
<212> TYPE: PRT
<213> ORGANISM: Pompilid sp.

<400> SEQUENCE: 135

Arg Leu Lys Leu Gly Leu Trp Asp Gln Leu Ser Arg Leu
1               5                   10

<210> SEQ ID NO 136
<211> LENGTH: 13
<212> TYPE: PRT
<213> ORGANISM: Pompilid sp.

<400> SEQUENCE: 136

Arg Leu Lys Leu Gly Ile Phe Asp Gln Leu Ser Arg Leu
1               5                   10

<210> SEQ ID NO 137
<211> LENGTH: 13
<212> TYPE: PRT
<213> ORGANISM: Pompilid sp.

<400> SEQUENCE: 137

Arg Leu Lys Leu Gly Ile Tyr Asp Gln Leu Ser Arg Leu
1               5                   10

<210> SEQ ID NO 138
<211> LENGTH: 13
<212> TYPE: PRT
<213> ORGANISM: Pompilid sp.

<400> SEQUENCE: 138

Arg Leu Lys Leu Gly Ile Trp Asp Gln Leu Ser Arg Leu
1               5                   10

<210> SEQ ID NO 139
<211> LENGTH: 13
<212> TYPE: PRT
<213> ORGANISM: Pompilid sp.

<400> SEQUENCE: 139

Arg Leu Arg Ile Gly Leu Phe Asp Gln Leu Ser Arg Leu
1               5                   10

<210> SEQ ID NO 140
<211> LENGTH: 13
<212> TYPE: PRT
<213> ORGANISM: Pompilid sp.

<400> SEQUENCE: 140

Arg Leu Arg Ile Gly Leu Tyr Asp Gln Leu Ser Arg Leu
1               5                   10

<210> SEQ ID NO 141
<211> LENGTH: 13
<212> TYPE: PRT
<213> ORGANISM: Pompilid sp.

<400> SEQUENCE: 141

Arg Leu Arg Ile Gly Leu Trp Asp Gln Leu Ser Arg Leu
1               5                   10

<210> SEQ ID NO 142
<211> LENGTH: 13
<212> TYPE: PRT
<213> ORGANISM: Pompilid sp.

<400> SEQUENCE: 142

Arg Leu Arg Ile Gly Ile Phe Asp Gln Leu Ser Arg Leu
1               5                   10

<210> SEQ ID NO 143
<211> LENGTH: 13
<212> TYPE: PRT
<213> ORGANISM: Pompilid sp.

<400> SEQUENCE: 143

Arg Leu Arg Ile Gly Ile Tyr Asp Gln Leu Ser Arg Leu
1               5                   10

<210> SEQ ID NO 144
<211> LENGTH: 13
<212> TYPE: PRT
<213> ORGANISM: Pompilid sp.

<400> SEQUENCE: 144

Arg Leu Arg Ile Gly Ile Trp Asp Gln Leu Ser Arg Leu
1               5                   10

```
<210> SEQ ID NO 145
<211> LENGTH: 13
<212> TYPE: PRT
<213> ORGANISM: Pompilid sp.

<400> SEQUENCE: 145

Arg Leu Arg Leu Gly Leu Phe Asp Gln Leu Ser Arg Leu
1               5                   10

<210> SEQ ID NO 146
<211> LENGTH: 13
<212> TYPE: PRT
<213> ORGANISM: Pompilid sp.

<400> SEQUENCE: 146

Arg Leu Arg Leu Gly Leu Tyr Asp Gln Leu Ser Arg Leu
1               5                   10

<210> SEQ ID NO 147
<211> LENGTH: 13
<212> TYPE: PRT
<213> ORGANISM: Pompilid sp.

<400> SEQUENCE: 147

Arg Leu Arg Leu Gly Leu Trp Asp Gln Leu Ser Arg Leu
1               5                   10

<210> SEQ ID NO 148
<211> LENGTH: 13
<212> TYPE: PRT
<213> ORGANISM: Pompilid sp.

<400> SEQUENCE: 148

Arg Leu Arg Leu Gly Ile Phe Asp Gln Leu Ser Arg Leu
1               5                   10

<210> SEQ ID NO 149
<211> LENGTH: 13
<212> TYPE: PRT
<213> ORGANISM: Pompilid sp.

<400> SEQUENCE: 149

Arg Leu Arg Leu Gly Ile Tyr Asp Gln Leu Ser Arg Leu
1               5                   10

<210> SEQ ID NO 150
<211> LENGTH: 13
<212> TYPE: PRT
<213> ORGANISM: Pompilid sp.

<400> SEQUENCE: 150

Arg Leu Arg Leu Gly Ile Trp Asp Gln Leu Ser Arg Leu
1               5                   10

<210> SEQ ID NO 151
<211> LENGTH: 13
<212> TYPE: PRT
<213> ORGANISM: Pompilid sp.

<400> SEQUENCE: 151

Lys Ile Lys Ile Gly Leu Phe Asp Gln Leu Ser Arg Leu
1               5                   10

<210> SEQ ID NO 152
<211> LENGTH: 13
```

<212> TYPE: PRT
<213> ORGANISM: Pompilid sp.

<400> SEQUENCE: 152

Lys Ile Lys Ile Gly Leu Tyr Asp Gln Leu Ser Arg Leu
1               5                   10

<210> SEQ ID NO 153
<211> LENGTH: 13
<212> TYPE: PRT
<213> ORGANISM: Pompilid sp.

<400> SEQUENCE: 153

Lys Ile Lys Ile Gly Leu Trp Asp Gln Leu Ser Arg Leu
1               5                   10

<210> SEQ ID NO 154
<211> LENGTH: 13
<212> TYPE: PRT
<213> ORGANISM: Pompilid sp.

<400> SEQUENCE: 154

Lys Ile Lys Ile Gly Ile Phe Asp Gln Leu Ser Arg Leu
1               5                   10

<210> SEQ ID NO 155
<211> LENGTH: 13
<212> TYPE: PRT
<213> ORGANISM: Pompilid sp.

<400> SEQUENCE: 155

Lys Ile Lys Ile Gly Ile Tyr Asp Gln Leu Ser Arg Leu
1               5                   10

<210> SEQ ID NO 156
<211> LENGTH: 13
<212> TYPE: PRT
<213> ORGANISM: Pompilid sp.

<400> SEQUENCE: 156

Lys Ile Lys Ile Gly Ile Trp Asp Gln Leu Ser Arg Leu
1               5                   10

<210> SEQ ID NO 157
<211> LENGTH: 13
<212> TYPE: PRT
<213> ORGANISM: Pompilid sp.

<400> SEQUENCE: 157

Lys Ile Lys Leu Gly Leu Phe Asp Gln Leu Ser Arg Leu
1               5                   10

<210> SEQ ID NO 158
<211> LENGTH: 13
<212> TYPE: PRT
<213> ORGANISM: Pompilid sp.

<400> SEQUENCE: 158

Lys Ile Lys Leu Gly Leu Tyr Asp Gln Leu Ser Arg Leu
1               5                   10

<210> SEQ ID NO 159
<211> LENGTH: 13
<212> TYPE: PRT
<213> ORGANISM: Pompilid sp.

<400> SEQUENCE: 159

Lys Ile Lys Leu Gly Leu Trp Asp Gln Leu Ser Arg Leu
1               5                   10

<210> SEQ ID NO 160
<211> LENGTH: 13
<212> TYPE: PRT
<213> ORGANISM: Pompilid sp.

<400> SEQUENCE: 160

Lys Ile Lys Leu Gly Ile Phe Asp Gln Leu Ser Arg Leu
1               5                   10

<210> SEQ ID NO 161
<211> LENGTH: 13
<212> TYPE: PRT
<213> ORGANISM: Pompilid sp.

<400> SEQUENCE: 161

Lys Ile Lys Leu Gly Ile Tyr Asp Gln Leu Ser Arg Leu
1               5                   10

<210> SEQ ID NO 162
<211> LENGTH: 13
<212> TYPE: PRT
<213> ORGANISM: Pompilid sp.

<400> SEQUENCE: 162

Lys Ile Lys Leu Gly Ile Trp Asp Gln Leu Ser Arg Leu
1               5                   10

<210> SEQ ID NO 163
<211> LENGTH: 13
<212> TYPE: PRT
<213> ORGANISM: Pompilid sp.

<400> SEQUENCE: 163

Lys Ile Arg Ile Gly Leu Phe Asp Gln Leu Ser Arg Leu
1               5                   10

<210> SEQ ID NO 164
<211> LENGTH: 13
<212> TYPE: PRT
<213> ORGANISM: Pompilid sp.

<400> SEQUENCE: 164

Lys Ile Arg Ile Gly Leu Tyr Asp Gln Leu Ser Arg Leu
1               5                   10

<210> SEQ ID NO 165
<211> LENGTH: 13
<212> TYPE: PRT
<213> ORGANISM: Pompilid sp.

<400> SEQUENCE: 165

Lys Ile Arg Ile Gly Leu Trp Asp Gln Leu Ser Arg Leu
1               5                   10

<210> SEQ ID NO 166
<211> LENGTH: 13
<212> TYPE: PRT
<213> ORGANISM: Pompilid sp.

<400> SEQUENCE: 166

Lys Ile Arg Ile Gly Ile Phe Asp Gln Leu Ser Arg Leu
1               5                   10

<210> SEQ ID NO 167
<211> LENGTH: 13
<212> TYPE: PRT
<213> ORGANISM: Pompilid sp.

<400> SEQUENCE: 167

Lys Ile Arg Ile Gly Ile Tyr Asp Gln Leu Ser Arg Leu
1               5                   10

<210> SEQ ID NO 168
<211> LENGTH: 13
<212> TYPE: PRT
<213> ORGANISM: Pompilid sp.

<400> SEQUENCE: 168

Lys Ile Arg Ile Gly Ile Trp Asp Gln Leu Ser Arg Leu
1               5                   10

<210> SEQ ID NO 169
<211> LENGTH: 13
<212> TYPE: PRT
<213> ORGANISM: Pompilid sp.

<400> SEQUENCE: 169

Lys Ile Arg Leu Gly Leu Phe Asp Gln Leu Ser Arg Leu
1               5                   10

<210> SEQ ID NO 170
<211> LENGTH: 13
<212> TYPE: PRT
<213> ORGANISM: Pompilid sp.

<400> SEQUENCE: 170

Lys Ile Arg Leu Gly Leu Tyr Asp Gln Leu Ser Arg Leu
1               5                   10

<210> SEQ ID NO 171
<211> LENGTH: 13
<212> TYPE: PRT
<213> ORGANISM: Pompilid sp.

<400> SEQUENCE: 171

Lys Ile Arg Leu Gly Leu Trp Asp Gln Leu Ser Arg Leu
1               5                   10

<210> SEQ ID NO 172
<211> LENGTH: 13
<212> TYPE: PRT
<213> ORGANISM: Pompilid sp.

<400> SEQUENCE: 172

Lys Ile Arg Leu Gly Ile Phe Asp Gln Leu Ser Arg Leu
1               5                   10

<210> SEQ ID NO 173
<211> LENGTH: 13
<212> TYPE: PRT
<213> ORGANISM: Pompilid sp.

<400> SEQUENCE: 173

Lys Ile Arg Leu Gly Ile Tyr Asp Gln Leu Ser Arg Leu

-continued

```
1               5                   10
```

<210> SEQ ID NO 174
<211> LENGTH: 13
<212> TYPE: PRT
<213> ORGANISM: Pompilid sp.

<400> SEQUENCE: 174

```
Lys Ile Arg Leu Gly Ile Trp Asp Gln Leu Ser Arg Leu
1               5                   10
```

<210> SEQ ID NO 175
<211> LENGTH: 13
<212> TYPE: PRT
<213> ORGANISM: Pompilid sp.

<400> SEQUENCE: 175

```
Lys Leu Lys Ile Gly Leu Phe Asp Gln Leu Ser Arg Leu
1               5                   10
```

<210> SEQ ID NO 176
<211> LENGTH: 13
<212> TYPE: PRT
<213> ORGANISM: Pompilid sp.

<400> SEQUENCE: 176

```
Lys Leu Lys Ile Gly Leu Tyr Asp Gln Leu Ser Arg Leu
1               5                   10
```

<210> SEQ ID NO 177
<211> LENGTH: 13
<212> TYPE: PRT
<213> ORGANISM: Pompilid sp.

<400> SEQUENCE: 177

```
Lys Leu Lys Ile Gly Leu Trp Asp Gln Leu Ser Arg Leu
1               5                   10
```

<210> SEQ ID NO 178
<211> LENGTH: 13
<212> TYPE: PRT
<213> ORGANISM: Pompilid sp.

<400> SEQUENCE: 178

```
Lys Leu Lys Ile Gly Ile Phe Asp Gln Leu Ser Arg Leu
1               5                   10
```

<210> SEQ ID NO 179
<211> LENGTH: 13
<212> TYPE: PRT
<213> ORGANISM: Pompilid sp.

<400> SEQUENCE: 179

```
Lys Leu Lys Ile Gly Ile Tyr Asp Gln Leu Ser Arg Leu
1               5                   10
```

<210> SEQ ID NO 180
<211> LENGTH: 13
<212> TYPE: PRT
<213> ORGANISM: Pompilid sp.

<400> SEQUENCE: 180

```
Lys Leu Lys Ile Gly Ile Trp Asp Gln Leu Ser Arg Leu
1               5                   10
```

```
<210> SEQ ID NO 181
<211> LENGTH: 13
<212> TYPE: PRT
<213> ORGANISM: Pompilid sp.

<400> SEQUENCE: 181

Lys Leu Lys Leu Gly Leu Phe Asp Gln Leu Ser Arg Leu
1               5                   10

<210> SEQ ID NO 182
<211> LENGTH: 13
<212> TYPE: PRT
<213> ORGANISM: Pompilid sp.

<400> SEQUENCE: 182

Lys Leu Lys Leu Gly Leu Tyr Asp Gln Leu Ser Arg Leu
1               5                   10

<210> SEQ ID NO 183
<211> LENGTH: 13
<212> TYPE: PRT
<213> ORGANISM: Pompilid sp.

<400> SEQUENCE: 183

Lys Leu Lys Leu Gly Leu Trp Asp Gln Leu Ser Arg Leu
1               5                   10

<210> SEQ ID NO 184
<211> LENGTH: 13
<212> TYPE: PRT
<213> ORGANISM: Pompilid sp.

<400> SEQUENCE: 184

Lys Leu Lys Leu Gly Ile Phe Asp Gln Leu Ser Arg Leu
1               5                   10

<210> SEQ ID NO 185
<211> LENGTH: 13
<212> TYPE: PRT
<213> ORGANISM: Pompilid sp.

<400> SEQUENCE: 185

Lys Leu Lys Leu Gly Ile Tyr Asp Gln Leu Ser Arg Leu
1               5                   10

<210> SEQ ID NO 186
<211> LENGTH: 13
<212> TYPE: PRT
<213> ORGANISM: Pompilid sp.

<400> SEQUENCE: 186

Lys Leu Lys Leu Gly Ile Trp Asp Gln Leu Ser Arg Leu
1               5                   10

<210> SEQ ID NO 187
<211> LENGTH: 13
<212> TYPE: PRT
<213> ORGANISM: Pompilid sp.

<400> SEQUENCE: 187

Lys Leu Arg Ile Gly Leu Phe Asp Gln Leu Ser Arg Leu
1               5                   10

<210> SEQ ID NO 188
```

```
<211> LENGTH: 13
<212> TYPE: PRT
<213> ORGANISM: Pompilid sp.

<400> SEQUENCE: 188

Lys Leu Arg Ile Gly Leu Tyr Asp Gln Leu Ser Arg Leu
1               5                   10

<210> SEQ ID NO 189
<211> LENGTH: 13
<212> TYPE: PRT
<213> ORGANISM: Pompilid sp.

<400> SEQUENCE: 189

Lys Leu Arg Ile Gly Leu Trp Asp Gln Leu Ser Arg Leu
1               5                   10

<210> SEQ ID NO 190
<211> LENGTH: 13
<212> TYPE: PRT
<213> ORGANISM: Pompilid sp.

<400> SEQUENCE: 190

Lys Leu Arg Ile Gly Ile Phe Asp Gln Leu Ser Arg Leu
1               5                   10

<210> SEQ ID NO 191
<211> LENGTH: 13
<212> TYPE: PRT
<213> ORGANISM: Pompilid sp.

<400> SEQUENCE: 191

Lys Leu Arg Ile Gly Ile Tyr Asp Gln Leu Ser Arg Leu
1               5                   10

<210> SEQ ID NO 192
<211> LENGTH: 13
<212> TYPE: PRT
<213> ORGANISM: Pompilid sp.

<400> SEQUENCE: 192

Lys Leu Arg Ile Gly Ile Trp Asp Gln Leu Ser Arg Leu
1               5                   10

<210> SEQ ID NO 193
<211> LENGTH: 13
<212> TYPE: PRT
<213> ORGANISM: Pompilid sp.

<400> SEQUENCE: 193

Lys Leu Arg Leu Gly Leu Phe Asp Gln Leu Ser Arg Leu
1               5                   10

<210> SEQ ID NO 194
<211> LENGTH: 13
<212> TYPE: PRT
<213> ORGANISM: Pompilid sp.

<400> SEQUENCE: 194

Lys Leu Arg Leu Gly Leu Tyr Asp Gln Leu Ser Arg Leu
1               5                   10

<210> SEQ ID NO 195
<211> LENGTH: 13
<212> TYPE: PRT
```

<213> ORGANISM: Pompilid sp.

<400> SEQUENCE: 195

Lys Leu Arg Leu Gly Leu Trp Asp Gln Leu Ser Arg Leu
1               5                   10

<210> SEQ ID NO 196
<211> LENGTH: 13
<212> TYPE: PRT
<213> ORGANISM: Pompilid sp.

<400> SEQUENCE: 196

Lys Leu Arg Leu Gly Ile Phe Asp Gln Leu Ser Arg Leu
1               5                   10

<210> SEQ ID NO 197
<211> LENGTH: 13
<212> TYPE: PRT
<213> ORGANISM: Pompilid sp.

<400> SEQUENCE: 197

Lys Leu Arg Leu Gly Ile Tyr Asp Gln Leu Ser Arg Leu
1               5                   10

<210> SEQ ID NO 198
<211> LENGTH: 13
<212> TYPE: PRT
<213> ORGANISM: Pompilid sp.

<400> SEQUENCE: 198

Lys Leu Arg Leu Gly Ile Trp Asp Gln Leu Ser Arg Leu
1               5                   10

<210> SEQ ID NO 199
<211> LENGTH: 11
<212> TYPE: PRT
<213> ORGANISM: Pompilid sp.
<220> FEATURE:
<221> NAME/KEY: MISC_FEATURE
<222> LOCATION: (1)..(1)
<223> OTHER INFORMATION: Arg or Lys
<221> NAME/KEY: MISC_FEATURE
<222> LOCATION: (2)..(2)
<223> OTHER INFORMATION: Ile or Leu
<221> NAME/KEY: MISC_FEATURE
<222> LOCATION: (3)..(3)
<223> OTHER INFORMATION: Arg or Lys
<221> NAME/KEY: MISC_FEATURE
<222> LOCATION: (4)..(4)
<223> OTHER INFORMATION: Ile or Leu
<221> NAME/KEY: MISC_FEATURE
<222> LOCATION: (6)..(6)
<223> OTHER INFORMATION: Ile or Leu
<221> NAME/KEY: MISC_FEATURE
<222> LOCATION: (7)..(7)
<223> OTHER INFORMATION: Phe, Tyr or Trp

<400> SEQUENCE: 199

Xaa Xaa Xaa Xaa Gly Xaa Xaa Asp Gln Leu Ser
1               5                   10

<210> SEQ ID NO 200
<211> LENGTH: 10
<212> TYPE: PRT
<213> ORGANISM: Pompilid sp.
<220> FEATURE:
<221> NAME/KEY: MISC_FEATURE
<222> LOCATION: (1)..(1)
<223> OTHER INFORMATION: Arg or Lys -continued

```
<221> NAME/KEY: MISC_FEATURE
<222> LOCATION: (2)..(2)
<223> OTHER INFORMATION: Ile or Leu
<221> NAME/KEY: MISC_FEATURE
<222> LOCATION: (3)..(3)
<223> OTHER INFORMATION: Arg or Lys
<221> NAME/KEY: MISC_FEATURE
<222> LOCATION: (4)..(4)
<223> OTHER INFORMATION: Ile or Leu
<221> NAME/KEY: MISC_FEATURE
<222> LOCATION: (6)..(6)
<223> OTHER INFORMATION: Ile or Leu
<221> NAME/KEY: MISC_FEATURE
<222> LOCATION: (7)..(7)
<223> OTHER INFORMATION: Phe, Tyr, or Trp

<400> SEQUENCE: 200

Xaa Xaa Xaa Xaa Gly Xaa Xaa Asp Gln Leu
1               5                  10

<210> SEQ ID NO 201
<211> LENGTH: 10
<212> TYPE: PRT
<213> ORGANISM: Pompilid sp.
<220> FEATURE:
<221> NAME/KEY: misc_feature
<222> LOCATION: (1)..(1)
<223> OTHER INFORMATION: Arg or Lys
<221> NAME/KEY: misc_feature
<222> LOCATION: (3)..(3)
<223> OTHER INFORMATION: Arg or Lys
<221> NAME/KEY: misc_feature
<222> LOCATION: (2)..(2)
<223> OTHER INFORMATION: Ile or Leu
<221> NAME/KEY: misc_feature
<222> LOCATION: (4)..(4)
<223> OTHER INFORMATION: Ile or Leu
<221> NAME/KEY: misc_feature
<222> LOCATION: (6)..(6)
<223> OTHER INFORMATION: Ile or Leu
<221> NAME/KEY: misc_feature
<222> LOCATION: (7)..(7)
<223> OTHER INFORMATION: Phe, Tyr or Trp
<221> NAME/KEY: misc_feature
<222> LOCATION: (10)..(10)
<223> OTHER INFORMATION: Leu or Leu, Ser or Leu, Ser, Lys or Leu, Ser,
      Arg or Leu, Ser, Lys, Leu or Leu, Ser, Arg, Leu

<400> SEQUENCE: 201

Xaa Xaa Xaa Xaa Gly Xaa Xaa Asp Gln Xaa
1               5                  10

<210> SEQ ID NO 202
<211> LENGTH: 13
<212> TYPE: PRT
<213> ORGANISM: Pompilid sp.

<400> SEQUENCE: 202

Arg Ile Lys Ile Gly Leu Phe Asp Gln Leu Ser Lys Leu
1               5                  10

<210> SEQ ID NO 203
<211> LENGTH: 13
<212> TYPE: PRT
<213> ORGANISM: Pompilid sp.

<400> SEQUENCE: 203

Arg Ile Lys Ile Gly Leu Phe Asp Gln Leu Ser Arg Leu
1               5                  10
```

POMPILID WASP-DERIVED NEUROPEPTIDES

This application is a 371 of PCT/JP98/03730, filed Aug. 24, 1998, which claims the priority of Japan JP9-241699, filed Aug. 25, 1997

TECHNICAL FIELD

The present invention relates to novel neuropeptides and more specifically to peptides obtained from the venoms of the solitary wasps *Anoplius samariensis* and *Batozonellus maculifrons*, and analogous peptides thereof.

BACKGROUND ART

Since solitary wasp species such as thread-waisted wasps and pompilid wasps paralyze other insects with their venom, it is believed that the venom contain substances that act on the nervous system. In fact, peptides called mastoparans have been isolated from a certain kind of solitary wasp, and these peptides are used as useful compounds for the study of information transmission system of the living body.

On the other hand, various compounds have been isolated in the studies on spider toxins, and it has been confirmed that their effect of paralyzing nerves is based on their inhibitory action on glutamate receptors. Glutamic acid is known to play an important role as an excitatory neurotransmitter mediated by glutamate receptors in the central nervous system (e.g. brain, spinal cord) of mammals, and the synapses of insects and crustaceans. And further, it is known that excess glutamic acid causes over-excitation of nerve cells resulting in death of the nerve cells. Therefore, enhancement of the function of glutamate receptors and conversely temporary blocking of their function are believed to provide therapeutic benefits on cerebral nerve diseases associated with glutamic acid.

DISCLOSURE OF THE INVENTION

Accordingly, the object of the present invention is to find, in the venom of the solitary wasps, substances that act on the glutamate receptor or substances that promote or inhibit the release of glutamic acid, and to apply them to medical therapeutic purposes.

In order to achieve the above object, the present inventors have isolated a peptide (1) represented by SEQ ID NO: 1:

and a peptide (97) represented by SEQ ID NO: 2:

from the venom sac extracts of solitary wasps *A. samariensis* and *B. maculifrons*, on the basis of the ability to enhance or block the neurotransmission through the neuron synapses of lobster's walking leg.

Furthermore, peptides related to the above peptides (1) and (97) were synthesized by the conventional solid phase method and their structure-activity relationship was examined. As a result, it was found that the peptides represented by the amino acid sequence formula (A):

wherein:

R is basically $NH_2$, which also may be -Leu-$NH_2$, -Leu-Ser-$NH_2$, -Leu-Ser-Lys-$NH_2$, -Leu-Ser-Arg-$NH_2$, -Leu-Ser-Lys-Leu-$NH_2$, (SEQ ID NO:3) or -Leu-Ser-Arg-Leu-$NH_2$ (SEQ ID NO:4), $X_1$ and $X_3$ are basic amino acid residues;

$X_2$, $X_4$ and $X_6$ are aliphatic amino acid residues; and $X_7$ is an aromatic amino acid residue, can show the above-mentioned activity.

The basic amino acid residues $X_1$ and $X_3$ include arginine or lysine residue, the aliphatic amino acid residues $X_2$, $X_4$ and $X_6$ include leucine or isoleucine residue, and the aromatic amino acid residue $X_7$ includes phenylalanine, tyrosine, or tryptophan residue.

Accordingly, the present invention provides, as a neuropeptide, a peptide represented by the amino acid sequence formula (A):

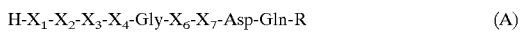

wherein:

each of $X_1$ and $X_3$ independently represents Arg or Lys, each of $X_2$, $X_4$ and $X_6$ independently represents Ile or Leu, and $X_7$ represents Phe, Tyr or Trp; and R represents —$NH_2$, -Leu-$NH_2$, -Leu-Ser-$NH_2$, -Leu-Ser-Lys-$NH_2$, -Leu-Ser-Arg-$NH_2$, -Leu-Ser-Lys-Leu-$NH_2$, (SEQ ID NO:3) or -Leu-Ser-Arg-Leu-$NH_2$ (SEQ ID NO:4);

and a salt thereof.

As an embodiment, the present invention provides a peptide represented by the amino acid sequence formula (B):

wherein:

each of $X_1$ and $X_3$ independently represents Arg or Lys, each of $X_2$, $X_4$ and $X_6$ independently represents Ile or Leu, and $X_7$ represents Phe, Tyr or Trp;

and a salt thereof.

As another embodiment, the present invention provides a peptide represented by the amino acid sequence formula (C):

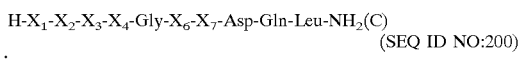

(SEQ ID NO:200)

wherein:

each of $X_1$ and $X_3$ independently represents Arg or Lys, each of $X_2$, $X_4$ and $X_6$ independently represents Ile or Leu, and $X_7$ represents Phe, Tyr or Trp;

and a salt thereof.

As a further embodiment, the present invention provides a peptide represented by the amino acid sequence formula (D):

(SEQ ID NO:199)

wherein:

each of $X_1$ and $X_3$ independently represents Arg or Lys, each of $X_2$, $X_4$ and $X_6$ independently represents Ile or Leu, and $X_7$ represents Phe, Tyr or Trp;

and a salt thereof.

As still another embodiment, the present invention provides a peptide represented by the amino acid sequence formula (E):

(SEQ ID NO:5)

wherein:

each of $X_1$ and $X_3$ independently represents Arg or Lys, each of $X_2$, $X_4$ and $X_6$ independently represents Ile or Leu, and $X_7$ represents Phe, Tyr or Trp;

and a salt thereof.

As still another embodiment, the present invention provides a peptide represented by the amino acid sequence formula (F):

H-X$_1$-X$_2$-X$_3$-X$_4$-Gly-X$_6$-X$_7$-Asp-Gln-Leu-Ser-Arg-NH$_2$(F)
(SEQ ID NO:6)

wherein:
each of X$_1$ and X$_3$ independently represents Arg or Lys, each of X$_2$, X$_4$ and X$_6$ independently represents Ile or Leu, and X$_7$ represents Phe, Tyr or Trp;
and a salt thereof.

As still another embodiment, the present invention provides a peptide represented by the amino acid sequence formula (G):

H-X$_1$-X$_2$-X$_3$-X$_4$-Gly-X$_6$-X$_7$-Asp-Gln-Leu-Ser-Lys-Leu-NH$_2$(G)
(SEQ ID NO:7)

wherein:
each of X$_1$ and X$_3$ independently represents Arg or Lys, each of X$_2$, X$_4$ and X$_6$ independently represents Ile or Leu, and X$_7$ represents Phe, Tyr or Trp;
and a salt thereof.

As still a further embodiment, the present invention provides a peptide represented by the amino acid sequence formula (H):

H-X$_1$-X$_2$-X$_3$-X$_4$-Gly-X$_6$-X$_7$-Asp-Gln-Leu-Ser-Arg-Leu-NH$_2$(H)
(SEQ ID NO:8)

wherein:
each of X$_1$ and X$_3$ independently represents Arg or Lys, each of X$_2$, X$_4$ and X$_6$ independently represents Ile or Leu, and X$_7$ represents Phe, Tyr or Trp;
and a salt thereof.

Among the above peptides provided by the present invention, the most preferred embodiment is a peptide represented by the amino acid sequence formula (1):

H-Arg-Ile-Lys-Ile-Gly-Leu-Phe-Asp-Gln-Leu-Ser-Lys-Leu-NH$_2$(1)
(SEQ ID NO:1)

and a salt thereof, or a peptide represented by the amino acid sequence formula (97):

H-Arg-Ile-Lys-Ile-Gly-Leu-Phe-Asp-Gln-Leu-Ser-Arg-Leu-NH$_2$(97)
(SEQ ID NO:2)

and a salt thereof.

As another embodiment, the present invention provides a pharmaceutical composition containing the peptide represented by the amino acid sequence formula (A) or a salt thereof for treatment of glutamate receptor related diseases.

As still another embodiment, the present invention provides use of the peptide represented by the amino acid sequence formula (A) or a salt thereof for treatment of glutamate receptor related diseases.

As still a further embodiment, the present invention provides a method for treatment of glutamate receptor related diseases which composing administering an effective amount of the peptide represented by the amino acid sequence formula (A) or a salt thereof.

BEST MODE FOR CARRYING OUT THE INVENTION

In the present specification and in each of the above formulae, Gly stands for a glycine residue, Asp stands for an aspartic acid residue, Gln stands for a glutamine residue, Arg stands for an arginine residue, Lys stands for a lysine residue, Ile stands for an isoleucine residue, Leu stands for a leucine residue, Phe stands for a phenylalanine residue, Tyr stands for a tyrosine residue, Trp stands for a tryptophan residue, and Ser stands for a serine residue. Amino acid sequences are indicated by the triplet code of IUPAC.

The peptides provided by the present invention include the following peptides:

H-Arg-Ile-Lys-Ile-Gly-Leu-Phe-Asp-Gln-Leu-Ser-Lys-Leu-NH$_2$ (1) (SEQ ID NO:1)
H-Arg-Ile-Lys-Ile-Gly-Leu-Tyr-Asp-Gln-Leu-Ser-Lys-Leu-NH$_2$ (2) (SEQ ID NO:9)
H-Arg-Ile-Lys-Ile-Gly-Leu-Trp-Asp-Gln-Leu-Ser-Lys-Leu-NH$_2$ (3) (SEQ ID NO:10)
H-Arg-Ile-Lys-Ile-Gly-Ile-Phe-Asp-Gln-Leu-Ser-Lys-Leu-NH$_2$ (4) (SEQ ID NO:11)
H-Arg-Ile-Lys-Ile-Gly-Ile-Tyr-Asp-Gln-Leu-Ser-Lys-Leu-NH$_2$ (5) (SEQ ID NO:12)
H-Arg-Ile-Lys-Ile-Gly-Ile-Trp-Asp-Gln-Leu-Ser-Lys-Leu-NH$_2$ (6) (SEQ ID NO:13)
H-Arg-Ile-Lys-Leu-Gly-Leu-Phe-Asp-Gln-Leu-Ser-Lys-Leu-NH$_2$ (7) (SEQ ID NO:14)
H-Arg-Ile-Lys-Leu-Gly-Leu-Tyr-Asp-Gln-Leu-Ser-Lys-Leu-NH$_2$ (8) (SEQ ID NO:15)
H-Arg-Ile-Lys-Leu-Gly-Leu-Trp-Asp-Gln-Leu-Ser-Lys-Leu-NH$_2$ (9) (SEQ ID NO:16)
H-Arg-Ile-Lys-Leu-Gly-leu-Phe-Asp-Gln-Leu-Ser-Lys-Leu-NH$_2$ (10) (SEQ ID NO:17)
H-Arg-Ile-Lys-Leu-Gly-Ile-Tyr-Asp-Gln-Leu-Ser-Lys-Leu-NH$_2$ (11) (SEQ ID NO:18)
H-Arg-Ile-Lys-Leu-Gly-Ile-Trp-Asp-Gln-Leu-Ser-Lys-Leu-NH$_2$ (12) (SEQ ID NO:19)
H-Arg-Ile-Arg-Ile-Gly-Leu-Phe-Asp-Gln-Leu-Ser-Lys-Leu-NH$_2$ (13) (SEQ ID NO:20)
H-Arg-Ile-Arg-Ile-Gly-Leu-Tyr-Asp-Gln-Leu-Ser-Lys-Leu-NH$_2$ (14) (SEQ ID NO:21)
H-Arg-Ile-Arg-Ile-Gly-Leu-Trp-Asp-Gln-Leu-Ser-Lys-Leu-NH$_2$ (15) (SEQ ID NO:22)
H-Arg-Ile-Arg-Ile-Gly-Ile-Phe-Asp-Gln-Leu-Ser-Lys-Leu-NH$_2$ (16) (SEQ ID NO:23)
H-Arg-Ile-Arg-Ile-Gly-Ile-Tyr-Asp-Gln-Leu-Ser-Lys-Leu-NH$_2$ (17) (SEQ ID NO:24)
H-Arg-Ile-Arg-Ile-Gly-Ile-Trp-Asp-Gln-Leu-Ser-Lys-Leu-NH$_2$ (18) (SEQ ID NO:25)
H-Arg-Ile-Arg-Leu-Gly-Leu-Phe-Asp-Gln-Leu-Ser-Lys-Leu-NH$_2$ (19) (SEQ ID NO:26)
H-Arg-Ile-Arg-Leu-Gly-Leu-Tyr-Asp-Gln-Leu-Ser-Lys-Leu-NH$_2$ (20) (SEQ ID NO:27)
H-Arg-Ile-Arg-Leu-Gly-Leu-Trp-Asp-Gln-Leu-Ser-Lys-Leu-NH$_2$ (21) (SEQ ID NO:28)
H-Arg-Ile-Arg-Leu-Gly-Ile-Phe-Asp-Gln-Leu-Ser-Lys-Leu-NH$_2$ (22) (SEQ ID NO:29)
H-Arg-Ile-Arg-Leu-Gly-Ile-Tyr-Asp-Gln-Leu-Ser-Lys-Leu-NH$_2$ (23) (SEQ ID NO:30)
H-Arg-Ile-Arg-Leu-Gly-Ile-Trp-Asp-Gln-Leu-Ser-Lys-Leu-NH$_2$ (24) (SEQ ID NO:31)
H-Arg-Leu-Lys-Ile-Gly-Leu-Phe-Asp-Gln-Leu-Ser-Lys-Leu-NH$_2$ (25) (SEQ ID NO:32)
H-Arg-Leu-Lys-Ile-Gly-Leu-Tyr-Asp-Gln-Leu-Ser-Lys-Leu-NH$_2$ (26) (SEQ ID NO:33)
H-Arg-Leu-Lys-Ile-Gly-Leu-Trp-Asp-Gln-Leu-Ser-Lys-Leu-NH$_2$ (27) (SEQ ID NO:34)
H-Arg-Leu-Lys-Ile-Gly-Ile-Phe-Asp-Gln-Leu-Ser-Lys-Leu-NH$_2$ (28) (SEQ ID NO:35)
H-Arg-Leu-Lys-Ile-Gly-Ile-Tyr-Asp-Gln-Leu-Ser-Lys-Leu-NH$_2$ (29) (SEQ ID NO:36)
H-Arg-Leu-Lys-Ile-Gly-Ile-Trp-Asp-Gln-Leu-Ser-Lys-Leu-NH$_2$ (30) (SEQ ID NO:37)
H-Arg-Leu-Lys-Leu-Gly-Leu-Phe-Asp-Gln-Leu-Ser-Lys-Leu-NH$_2$ (31) (SEQ ID NO:38)

H-Arg-Leu-Lys-Leu-Gly-Leu-Tyr-Asp-Gln-Leu-Ser-Lys-Leu-NH₂ (32) (SEQ ID NO:39)
H-Arg-Leu-Lys-Leu-Gly-Leu-Trp-Asp-Gln-Leu-Ser-Lys-Leu-NH₂ (33) (SEQ ID NO:40)
H-Arg-Leu-Lys-Leu-Gly-Ile-Phe-Asp-Gln-Leu-Ser-Lys-Leu-NH₂ (34) (SEQ ID NO:41)
H-Arg-Leu-Lys-Leu-Gly-Ile-Tyr-Asp-Gln-Leu-Ser-Lys-Leu-NH₂ (35) (SEQ ID NO:42)
H-Arg-Leu-Lys-Leu-Gly-Ile-Trp-Asp-Gln-Leu-Ser-Lys-Leu-NH₂ (36) (SEQ ID NO:43)
H-Arg-Leu-Arg-Ile-Gly-Leu-Phe-Asp-Gln-Leu-Ser-Lys-Leu-NH₂ (37) (SEQ ID NO:44)
H-Arg-Leu-Arg-Ile-Gly-Leu-Tyr-Asp-Gln-Leu-Ser-Lys-Leu-NH₂ (38) (SEQ ID NO:45)
H-Arg-Leu-Arg-Ile-Gly-Leu-Trp-Asp-Gln-Leu-Ser-Lys-Leu-NH₂ (39) (SEQ ID NO:46)
H-Arg-Leu-Arg-Ile-Gly-Ile-Phe-Asp-Gln-Leu-Ser-Lys-Leu-NH₂ (40) (SEQ ID NO:47)
H-Arg-Leu-Arg-Ile-Gly-Ile-Tyr-Asp-Gln-Leu-Ser-Lys-Leu-NH₂ (41) (SEQ ID NO:48)
H-Arg-Leu-Arg-Ile-Gly-Ile-Trp-Asp-Gln-Leu-Ser-Lys-Leu-NH₂ (42) (SEQ ID NO:49)
H-Arg-Leu-Arg-Leu-Gly-Leu-Phe-Asp-Gln-Leu-Ser-Lys-Leu-NH₂ (43) (SEQ ID NO:50)
H-Arg-Leu-Arg-Leu-Gly-Leu-Tyr-Asp-Gln-Leu-Ser-Lys-Leu-NH₂ (44) (SEQ ID NO:51)
H-Arg-Leu-Arg-Leu-Gly-Leu-Trp-Asp-Gln-Leu-Ser-Lys-Leu-MH₂ (45) (SEQ ID NO:52)
H-Arg-Leu-Arg-Leu-Gly-Ile-Phe-Asp-Gln-Leu-Ser-Lys-Leu-NH₂ (46) (SEQ ID NO:53)
H-Arg-Leu-Arg-Leu-Gly-Ile-Tyr-Asp-Gln-Leu-Ser-Lys-Leu-NH₂ (47) (SEQ ID NO:54)
H-Arg-Leu-Arg-Leu-Gly-Ile-Trp-Asp-Gln-Leu-Ser-Lys-Leu-NH₂ (48) (SEQ ID NO:55)
H-Lys-Ile-Lys-Ile-Gly-Leu-Phe-Asp-Gln-Leu-Ser-Lys-Leu-NH₂ (49) (SEQ ID NO:56)
H-Lys-Ile-Lys-Ile-Gly-Leu-Tyr-Asp-Gln-Leu-Ser-Lys-Leu-NH₂ (50) (SEQ ID NO:57)
H-Lys-Ile-Lys-Ile-Gly-Leu-Trp-Asp-Gln-Leu-Ser-Lys-Leu-NH₂ (51) (SEQ ID NO:58)
H-Lys-Ile-Lys-Ile-Gly-Ile-Phe-Asp-Gln-Leu-Ser-Lys-Leu-NH₂ (52) (SEQ ID NO:59)
H-Lys-Ile-Lys-Ile-Gly-Ile-Tyr-Asp-Gln-Leu-Ser-Lys-Leu-NH₂ (53) (SEQ ID NO:60)
H-Lys-Ile-Lys-Ile-Gly-Ile-Trp-Asp-Gln-Leu-Ser-Lys-Leu-NH₂ (54) (SEQ ID NO:61)
H-Lys-Ile-Lys-Leu-Gly-Leu-Phe-Asp-Gln-Leu-Ser-Lys-Leu-NH₂ (55) (SEQ ID NO:62)
H-Lys-Ile-Lys-Leu-Gly-Leu-Tyr-Asp-Gln-Leu-Ser-Lys-Leu-NH₂ (56) (SEQ ID NO:63)
H-Lys-Ile-Lys-Leu-Gly-Leu-Trp-Asp-Gln-Leu-Ser-Lys-Leu-NH₂ (57) (SEQ ID NO:64)
H-Lys-Ile-Lys-Leu-Gly-Ile-Phe-Asp-Gln-Leu-Ser-Lys-Leu NH₂ (58) (SEQ ID NO:65)
H-Lys-Ile-Lys-Leu-Gly-Ile-Tyr-Asp-Gln-Leu-Ser-Lys-Leu-NH₂ (59) (SEQ ID NO:66)
H-Lys-Ile-Lys-Leu-Gly-Ile-Trp-Asp-Gln-Leu-Ser-Lys-Leu-NH₂ (60) (SEQ ID NO:67)
H-Lys-Ile-Arg-Ile-Gly-Leu-Phe-Asp-Gln-Leu-Ser-Lys-Leu-NH₂ (61) (SEQ ID NO:68)
H-Lys-Ile-Arg-Ile-Gly-Leu-Tyr-Asp-Gln-Leu-Ser-Lys-Leu-NH₂ (62) (SEQ ID NO:69)
H-Lys-Ile-Arg-Ile-Gly-Leu-Trp-Asp-Gln-Leu-Ser-Lys-Leu-NH₂ (63) (SEQ ID NO:70)
H-Lys-Ile-Arg-Ile-Gly-Ile-Phe-Asp-Gln-Leu-Ser-Lys-Leu-NH₂ (64) (SEQ ID NO:71)
H-Lys-Ile-Arg-Ile-Gly-Ile-Tyr-Asp-Gln-Leu-Ser-Lys-Leu-NH₂ (65) (SEQ ID NO:72)
H-Lys-Ile-Arg-Ile-Gly-Ile-Trp-Asp-Gln-Leu-Ser-Lys-Leu-NH₂ (66) (SEQ ID NO:73)
H-Lys-Ile-Arg-Leu-Gly-Leu-Phe-Asp-Gln-Leu-Ser-Lys-Leu-NH₂ (67) (SEQ ID NO:74)
H-Lys-Ile-Arg-Leu-Gly-Leu-Tyr-Asp-Gln-Leu-Ser-Lys-Leu-NH₂ (68) (SEQ ID NO:75)
H-Lys-Ile-Arg-Leu-Gly-Leu-Trp-Asp-Gln-Leu-Ser-Lys-Leu-NH₂ (69) (SEQ ID NO:76)
H-Lys-Ile-Arg-Leu-Gly-Ile-Phe-Asp-Gln-Leu-Ser-Lys-Leu-NH₂ (70) (SEQ ID NO:77)
H-Lys-Ile-Arg-Leu-Gly-Ile-Tyr-Asp-Gln-Leu-Ser-Lys-Leu-NH₂ (71) (SEQ ID NO:78)
H-Lys-Ile-Arg-Leu-Gly-Ile-Trp-Asp-Gln-Leu-Ser-Lys-Leu-NH₂ (72) (SEQ ID NO:79)
H-Lys-Leu-Lys-Ile-Gly-Leu-Phe-Asp-Gln-Leu-Ser-Lys-Leu-NH₂ (73) (SEQ ID NO:80)
H-Lys-Leu-Lys-Ile-Gly-Leu-Tyr-Asp-Gln-Leu-Ser-Lys-Leu-NH₂ (74) (SEQ ID NO:81)
H-Lys-Leu-Lys-Ile-Gly-Leu-Trp-Asp-Gln-Leu-Ser-Lys-Leu-NH₂ (75) (SEQ ID NO:82)
H-Lys-Leu-Lys-Ile-Gly-Ile-Phe-Asp-Gln-Leu-Ser-Lys-Leu-NH₂ (76) (SEQ ID NO:83)
H-Lys-Leu-Lys-Ile-Gly-Ile-Tyr-Asp-Gln-Leu-Ser-Lys-Leu-NH₂ (77) (SEQ ID NO:84)
H-Lys-Leu-Lys-Ile-Gly-Ile-Trp-Asp-Gln-Leu-Ser-Lys-Leu-NH₂ (78) (SEQ ID NO:85)
H-Lys-Leu-Lys-Leu-Gly-Leu-Phe-Asp-Gln-Leu-Ser-Lys-Leu-NH₂ (79) (SEQ ID NO:86)
H-Lys-Leu-Lys-Leu-Gly-Leu-Tyr-Asp-Gln-Leu-Ser-Lys-Leu-NH₂ (80) (SEQ ID NO:87)
H-Lys-Leu-Lys-Leu-Gly-Leu-Trp-Asp-Gln-Leu-Ser-Lys-Leu-NH₂ (81) (SEQ ID NO:88)
H-Lys-Leu-Lys-Leu-Gly-Ile-Phe-Asp-Gln-Leu-Ser-Lys-Leu-NH₂ (82) (SEQ ID NO:89)
H-Lys-Leu-Lys-Leu-Gly-Ile-Tyr-Asp-Gln-Leu-Ser-Lys-Leu-NH₂ (83) (SEQ ID NO:90)
H-Lys-Leu-Lys-Leu-Gly-Ile-Trp-Asp-Gln-Leu-Ser-Lys-Leu-NH₂ (84) (SEQ ID NO:91)
H-Lys-Leu-Arg-Ile-Gly-Leu-Phe-Asp-Gln-Leu-Ser-Lys-Leu-NH₂ (85) (SEQ ID NO:92)
H-Lys-Leu-Arg-Ile-Gly-Leu-Tyr-Asp-Gln-Leu-Ser-Lys-Leu-NH₂ (86) (SEQ ID NO:93)
H-Lys-Leu-Arg-Ile-Gly-Leu-Trp-Asp-Gln-Leu-Ser-Lys-Leu-NH₂ (87) (SEQ ID NO:94)
H-Lys-Leu-Arg-Ile-Gly-Ile-Phe-Asp-Gln-Leu-Ser-Lys-Leu-NH₂ (88) (SEQ ID NO:95)
H-Lys-Leu-Arg-Ile-Gly-Ile-Tyr-Asp-Gln-Leu-Ser-Lys-Leu-NH₂ (89) (SEQ ID NO:96)
H-Lys-Leu-Arg-Ile-Gly-Ile-Trp-Asp-Gln-Leu-Ser-Lys-Leu-NH₂ (90) (SEQ ID NO:97)
H-Lys-Leu-Arg-Leu-Gly-Leu-Phe-Asp-Gln-Leu-Ser-Lys-Leu-NH₂ (91) (SEQ ID NO:98)
H-Lys-Leu-Arg-Leu-Gly-Leu-Tyr-Asp-Gln-Leu-Ser-Lys-Leu-NH₂ (92) (SEQ ID NO:99)
H-Lys-Leu-Arg-Leu-Gly-Leu-Trp-Asp-Gln-Leu-Ser-Lys-Leu-NH₂ (93) (SEQ ID NO:100)
H-Lys-Leu-Arg-Leu-Gly-Ile-Phe-Asp-Gln-Leu-Ser-Lys-Leu-NH₂ (94) (SEQ ID NO:101)
H-Lys-Leu-Arg-Leu-Gly-Ile-Tyr-Asp-Gln-Leu-Ser-Lys-Leu-NH₂ (95) (SEQ ID NO:102)
H-Lys-Leu-Arg-Leu-Gly-Ile-Trp-Asp-Gln-Leu-Ser-Lys-Leu-NH₂ (96) (SEQ ID NO:103)
H-Arg-Ile-Lys-Ile-Gly-Leu-Phe-Asp-Gln-Leu-Ser-Arg-Leu-NH₂ (97) (SEQ ID NO:104)
H-Arg-Ile-Lys-Ile-Gly-Leu-Tyr-Asp-Gln-Leu-Ser-Arg-Leu-NH₂ (98) (SEQ ID NO:105)
H-Arg-Ile-Lys-Ile-Gly-Leu-Trp-Asp-Gln-Leu-Ser-Arg-Leu-NH₂ (99) (SEQ ID NO:106)

H-Arg-Ile-Lys-Ile-Gly-Ile-Phe-Asp-Gln-Leu-Ser-Arg-Leu-NH₂ (100) (SEQ ID NO:107)
H-Arg-Ile-Lys-Ile-Gly-Ile-Tyr-Asp-Gln-Leu-Ser-Arg-Leu-NH₂ (101) (SEQ ID NO:108)
H-Arg-Ile-Lys-Ile-Gly-Ile-Trp-Asp-Gln-Leu-Ser-Arg-Leu-NH₂ (102) (SEQ ID NO:109)
H-Arg-Ile-Lys-Leu-Gly-Leu-Phe-Asp-Gln-Leu-Ser-Arg-Leu-NH₂ (103) (SEQ ID NO:110)
H-Arg-Ile-Lys-Leu-Gly-Leu-Tyr-Asp-Gln-Leu-Ser-Arg-Leu-NH₂ (104) (SEQ ID NO:111)
H-Arg-Ile-Lys-Leu-Gly-Leu-Trp-Asp-Gln-Leu-Ser-Arg-Leu-NH₂ (105) (SEQ ID NO:112)
H-Arg-Ile-Lys-Leu-Gly-Ile-Phe-Asp-Gln-Leu-Ser-Arg-Leu-NH₂ (106) (SEQ ID NO:113)
H-Arg-Ile-Lys-Leu-Gly-Ile-Tyr-Asp-Gln-Leu-Ser-Arg-Leu-NH₂ (107) (SEQ ID NO:114)
H-Arg-Ile-Lys-Leu-Gly-Ile-Trp-Asp-Gln-Leu-Ser-Arg-Leu-NH₂ (108) (SEQ ID NO:115)
H-Arg-Ile-Arg-Ile-Gly-Leu-Phe-Asp-Gln-Leu-Ser-Arg-Leu-NH₂ (109) (SEQ ID NO:116)
H-Arg-Ile-Arg-Ile-Gly-Leu-Tyr-Asp-Gln-Leu-Ser-Arg-Leu-NH₂ (110) (SEQ ID NO:117)
H-Arg-Ile-Arg-Ile-Gly-Leu-Trp-Asp-Gln-Leu-Ser-Arg-Leu-NH₂ (111) (SEQ ID NO:118)
H-Arg-Ile-Arg-Ile-Gly-Ile-Phe-Asp-Gln-Leu-Ser-Arg-Leu-NH₂ (112) (SEQ ID NO:119)
H-Arg-Ile-Arg-Ile-Gly-Ile-Tyr-Asp-Gln-Leu-Ser-Arg-Leu-NH₂ (113) (SEQ ID NO:120)
H-Arg-Ile-Arg-Ile-Gly-Ile-Trp-Asp-Gln-Leu-Ser-Arg-Leu-NH₂ (114) (SEQ ID NO:121)
H-Arg-Ile-Arg-Leu-Gly-Leu-Phe-Asp-Gln-Leu-Ser-Arg-Leu-NH₂ (115) (SEQ ID NO:122)
H-Arg-Ile-Arg-Leu-Gly-Leu-Tyr-Asp-Gln-Leu-Ser-Arg-Leu-NH₂ (116) (SEQ ID NO:123)
H-Arg-Ile-Arg-Leu-Gly-Leu-Trp-Asp-Gln-Leu-Ser-Arg-Leu-NH₂ (117) (SEQ ID NO:124)
H-Arg-Ile-Arg-Leu-Gly-Ile-Phe-Asp-Gln-Leu-Ser-Arg-Leu-NH₂ (118) (SEQ ID NO:125)
H-Arg-Ile-Arg-Leu-Gly-Ile-Tyr-Asp-Gln-Leu-Ser-Arg-Let-NH₂ (119) (SEQ ID NO:126)
H-Arg-Ile-Arg-Leu-Gly-Ile-Trp-Asp-Gln-Leu-Ser-Arg-Leu-NH₂ (120) (SEQ ID NO:127)
H-Arg-Leu-Lys-Ile-Gly-Leu-Phe-Asp-Gln-Leu-Ser-Arg-Leu-NH₂ (121) (SEQ ID NO:128)
H-Arg-Leu-Lys-Ile-Gly-Leu-Tyr-Asp-Gln-Leu-Ser-Arg-Leu-NH₂ (122) (SEQ ID NO:129)
H-Arg-Leu-Lys-Ile-Gly-Leu-Trp-Asp-Gln-Leu-Ser-Arg-Leu-NH₂ (123) (SEQ ID NO:130)
H-Arg-Leu-Lys-Ile-Gly-Leu-Phe-Asp-Gln-Leu-Ser-Arg-Leu-NH₂ (124) (SEQ ID NO:131)
H-Arg-Leu-Lys-Ile-Gly-Ile-Tyr-Asp-Gln-Leu-Ser-Arg-Leu-NH₂ (125) (SEQ ID NO:132)
H-Arg-Leu-Lys-Ile-Gly-Ile-Trp-Asp-Gln-Leu-Ser-Arg-Leu-NH₂ (126) (SEQ ID NO:133)
H-Arg-Leu-Lys-Ile-Gly-Ile-Phe-Asp-Gln-Leu-Ser-Arg-Leu-NH₂ (127) (SEQ ID NO:134)
H-Arg-Leu-Lys-Leu-Gly-Leu-Tyr-Asp-Gln-Leu-Ser-Arg-Leu-NH₂ (128) (SEQ ID NO:135)
H-Arg-Leu-Lys-Leu-Gly-Leu-Trp-Asp-Gln-Leu-Ser-Arg-Leu-NH₂ (129) (SEQ ID NO:136)
H-Arg-Leu-Lys-Leu-Gly-Leu-Phe-Asp-Gln-Leu-Ser-Arg-Leu-NH₂ (130) (SEQ ID NO:137)
H-Arg-Leu-Lys-Leu-Gly-Ile-Tyr-Asp-Gln-Leu-Ser-Arg-Leu-NH₂ (131) (SEQ ID NO:138)
H-Arg-Leu-Lys-Leu-Gly-Ile-Trp-Asp-Gln-Leu-Ser-Arg-Leu-NH₂ (132) (SEQ ID NO:139)
H-Arg-Leu-Lys-Leu-Gly-LIe-Phe-Asp-Gln-Leu-Ser-Arg-Leu-NH₂ (133) (SEQ ID NO:140)
H-Arg-Leu-Arg-Ile-Gly-Leu-Tyr-Asp-Gln-Leu-Ser-Arg-Leu-NH₂ (134) (SEQ ID NO:141)
H-Arg-Leu-Arg-Ile-Gly-Leu-Trp-Asp-Gln-Leu-Ser-Arg-Leu-NH₂ (135) (SEQ ID NO:142)
H-Arg-Leu-Arg-Ile-Gly-Leu-Phe-Asp-Gln-Leu-Ser-Arg-Leu-NH₂ (136) (SEQ ID NO:143)
H-Arg-Leu-Arg-Ile-Gly-Ile-Tyr-Asp-Gln-Leu-Ser-Arg-Leu-NH₂ (137) (SEQ ID NO:144)
H-Arg-Leu-Arg-Ile-Gly-Ile-Trp-Asp-Gln-Leu-Ser-Arg-Leu-NH₂ (138) (SEQ ID NO:145)
H-Arg-Leu-Arg-Ile-Gly-Ile-Phe-Asp-Gln-Leu-Ser-Arg-Leu-NH₂ (139) (SEQ ID NO:146)
H-Arg-Leu-Arg-Leu-Gly-Leu-Tyr-Asp-Gln-Leu-Ser-Arg-Leu-NH₂ (140) (SEQ ID NO:147)
H-Arg-Leu-Arg-Leu-Gly-Leu-Trp-Asp-Gln-Leu-Ser-Arg-Leu-NH₂ (141) (SEQ ID NO:148)
H-Arg-Leu-Arg-Leu-Gly-Leu-Phe-Asp-Gln-Leu-Ser-Arg-Leu-NH₂ (142) (SEQ ID NO:149)
H-Arg-Leu-Arg-Leu-Gly-Ile-Tyr-Asp-Gln-Leu-Ser-Arg-Leu-NH₂ (143) (SEQ ID NO:150)
H-Arg-Leu-Arg-Leu-Gly-Ile-Trp-Asp-Gln-Leu-Ser-Arg-Leu-NH₂ (144) (SEQ ID NO:151)
H-Lys-Ile-Lys-Ile-Gly-Leu-Phe-Asp-Gln-Leu-Ser-Arg-Leu-NH₂ (145) (SEQ ID NO:152)
H-Lys-Ile-Lys-Ile-Gly-Leu-Tyr-Asp-Gln-Leu-Ser-Arg-Leu-NH₂ (146) (SEQ ID NO:153)
H-Lys-Ile-Lys-Ile-Gly-Leu-Trp-Asp-Gln-Leu-Ser-Arg-Leu-NH₂ (147) (SEQ ID NO:154)
H-Lys-Ile-Lys-Ile-Gly-Ile-Phe-Asp-Gln-Leu-Ser-Arg-Leu-NH₂ (148) (SEQ ID NO:155)
H-Lys-Ile-Lys-Ile-Gly-Ile-Tyr-Asp-Gln-Leu-Ser-Arg-Leu-NH₂ (149) (SEQ ID NO:156)
H-Lys-Ile-Lys-Ile-Gly-Ile-Trp-Asp-Gln-Leu-Ser-Arg-Leu-NH₂ (150) (SEQ ID NO:157)
H-Lys-Ile-Lys-Leu-Gly-Leu-Phe-Asp-Gln-Leu-Ser-Arg-Leu-NH₂ (151) (SEQ ID NO:158)
H-Lys-Ile-Lys-Leu-Gly-Leu-Tyr-Asp-Gln-Leu-Ser-Arg-Leu-NH₂ (152) (SEQ ID NO:159)
H-Lys-Ile-Lys-Leu-Gly-Leu-Trp-Asp-Gln-Leu-Ser-Arg-Leu-NH₂ (153) (SEQ ID NO:160)
H-Lys-Ile-Lys-Leu-Gly-Ile-Phe-Asp-Gln-Leu-Ser-Arg-Leu-NH₂ (154) (SEQ ID NO:161)
H-Lys-Ile-Lys-Leu-Gly-Ile-Tyr-Asp-Gln-Leu-Ser-Arg-Leu-NH₂ (155) (SEQ ID NO:162)
H-Lys-Ile-Lys-Leu-Gly-Ile-Trp-Asp-Gln-Leu-Ser-Arg-Leu-NH₂ (156) (SEQ ID NO:163)
H-Lys-Ile-Arg-Ile-Gly-Leu-Phe-Asp-Gln-Leu-Ser-Arg-Leu-NH₂ (157) (SEQ ID NO:164)
H-Lys-Ile-Arg-Ile-Gly-Leu-Tyr-Asp-Gln-Leu-Ser-Arg-Leu-NH₂ (158) (SEQ ID NO:165)
H-Lys-Ile-Arg-Ile-Gly-Leu-Trp-Asp-Gln-Leu-Ser-Arg-Leu-NH₂ (159) (SEQ ID NO:166)
H-Lys-Ile-Arg-Ile-Gly-ILe-Phe-Asp-Gln-Leu-Ser-Arg-Leu-NH₂ (160) (SEQ ID NO:167)
H-Lys-Ile-Arg-Ile-Gly-Ile-Tyr-Asp-Gln-Leu-Ser-Arg-Leu-NH₂ (161) (SEQ ID NO:168)
H-Lys-Ile-Arg-Ile-Gly-Ile-Trp-Asp-Gln-Leu-Ser-Arg-Leu NH₂ (162) (SEQ ID NO:169)
H-Lys-Ile-Arg-Leu-Gly-Leu-Phe-Asp-Gln-Leu-Ser-Arg-Leu-NH₂ (163) (SEQ ID NO:170)
H-Lys-Ile-Arg-Leu-Gly-Leu-Tyr-Asp-Gln-Leu-Ser-Arg-Leu-NH₂ (164) (SEQ ID NO:171)
H-Lys-Ile-Arg-Leu-Gly-Leu-Trp-Asp-Gln-Leu-Ser-Arg-Leu-NH₂ (165) (SEQ ID NO:172)
H-Lys-Ile-Arg-Leu-Gly-Ile-Phe-Asp-Gln-Leu-Ser-Arg-Leu-NH₂ (166) (SEQ ID NO:173)
H-Lys-Ile-Arg-Leu-Gly-LIe-Tyr-Asp-Gln-Leu-Ser-Arg-Leu-NH₂ (167) (SEQ ID NO:174)

H-Lys-Ile-Arg-Leu-Gly-Ile-Trp-Asp-Gln-Leu-Ser-Arg-Leu-NH$_2$ (168) (SEQ ID NO:175)
H-Lys-Leu-Lys-ILe-Gly-Leu-Phe-Asp-Gln-Leu-Ser-Arg-Leu-NH$_2$ (169) (SEQ ID NO:176)
H-Lys-Leu-Lys-Ile-Gly-Leu-Tyr-Asp-Gln-Leu-Ser-Arg-Leu-NH$_2$ (170) (SEQ ID NO:177)
H-Lys-Leu-Lys-Ile-Gly-Leu-Trp-Asp-Gln-Leu-Ser-Arg-Leu-NH$_2$ (171) (SEQ ID NO:178)
H-Lys-Leu-Lys-Ile-Gly-Ile-Phe-Asp-Gln-Leu-Ser-Arg-Leu-NH$_2$ (172) (SEQ ID NO:179)
H-Lys-Leu-Lys-Ile-Gly-Leu-Tyr-Asp-Gln-Leu-Ser-Arg-Leu-NH$_2$ (173) (SEQ ID NO:180)
H-Lys-Leu-Lys-Ile-Gly-Ile-Trp-Asp-Gln-Leu-Ser-Arg-Leu-NH$_2$ (174) (SEQ ID NO:181)
H-Lys-Leu-Lys-Leu-Gly-Leu-Phe-Asp-Gln-Leu-Ser-Arg-Leu-NH$_2$ (175) (SEQ ID NO:182)
H-Lys-Leu-Lys-Leu-Gly-Leu-Tyr-Asp-Gln-Leu-Ser-Arg-Leu-NH$_2$ (176) (SEQ ID NO:183)
H-Lys-Leu-Lys-Leu-Gly-Leu-Trp-Asp-Gln-Leu-Ser-Arg-Leu-NH$_2$ (177) (SEQ ID NO:184)
H-Lys-Leu-Lys-Leu-Gly-Ile-Phe-Asp-Gln-Leu-Ser-Arg-Leu-NH$_2$ (178) (SEQ ID NO:185)
H-Lys-Leu-Lys-Leu-Gly-Ile-Tyr-Asp-Gln-Leu-Ser-Arg-Leu-NH$_2$ (179) (SEQ ID NO:186)
H-Lys-Leu-Lys-Leu-Gly-Ile-Trp-Asp-Gln-Leu-Ser-Arg-Leu-NH$_2$ (180) (SEQ ID NO:187)
H-Lys-Leu-Arg-Ile-Gly-Leu-Phe-Asp-Gln-Leu-Ser-Arg-Leu-NH$_2$ (181) (SEQ ID NO:188)
H-Lys-Leu-Arg-Ile-Gly-Leu-Tyr-Asp-Gln-Leu-Ser-Arg-Leu-NH$_2$ (182) (SEQ ID NO:189)
H-Lys-Leu-Arg-Ile-Gly-Leu-Trp-Asp-Gln-Leu-Ser-Arg-Leu-NH$_2$ (183) (SEQ ID NO:190)
H-Lys-Leu-Arg-Ile-Gly-Leu-Phe-Asp-Gln-Leu-Ser-Arg-Leu-NH$_2$ (184) (SEQ ID NO:191)
H-Lys-Leu-Arg-Ile-Gly-Ile-Tyr-Asp-Gln-Leu-Ser-Arg-Leu-NH$_2$ (185) (SEQ ID NO:192)
H-Lys-Leu-Arg-ILe-Gly-Leu-Trp-Asp-Gln-Leu-Ser-Arg-Leu-NH$_2$ (186) (SEQ ID NO:193)
H-Lys-Leu-Arg-Ile-Gly-Ile-Phe-Asp-Gln-Leu-Ser-Arg-Leu-NH$_2$ (187) (SEQ ID NO:194)
H-Lys-Leu-Arg-Leu-Gly-Leu-Tyr-Asp-Gln-Leu-Ser-Arg-Leu-NH$_2$ (188) (SEQ ID NO:195)
H-Lys-Leu-Arg-Leu-Gly-Leu-Trp-Asp-Gln-Leu-Ser-Arg-Leu-NH$_2$ (189) (SEQ ID NO:196)
H-Lys-Leu-Arg-Leu-Gly-Leu-Phe-Asp-Gln-Leu-Ser-Arg-Leu-NH$_2$ (190) (SEQ ID NO:197)
H-Lys-Leu-Arg-Leu-Gly-Ile-Tyr-Asp-Gln-Leu-Ser-Arg-Leu-NH$_2$ (191) (SEQ ID NO:198)
H-Lys-Leu-Arg-Leu-Gly-Ile-Trp-Asp-Gln-Leu-Ser-Arg-Leu-NH$_2$ (192) (SEQ ID NO:199)

In order to obtain the peptides of the present invention, for example, venom sac of a solitary wasp containing said peptides may be excised and then homogenized in a water-containing organic solvent, and the resulting homogenate may be centrifuged to obtain a supernatant, which may be purified by a reversed phase chromatography until finally it exhibits a single peak when monitored by UV absorbance at 215 nm, thereby isolating and purifying the desired compound.

The water-containing organic solvent to be used for the homogenization during the above purification process means a mixture of water and an organic solvent that is freely miscible with water, and may be any solvent which permits extraction of the compound of the present invention. Examples include, but not limited to, water-containing acetone, water-containing acetonitrile, and the like. When the resulting supernatant is directly applied to the reversed phase chromatography, it is preferred that about 0.1% of trifluoroacetic acid (hereinafter referred to as TFA) is added to such a water-containing organic solvent.

Since the peptides provided by the present invention consist of at most about 13 amino acids, they can be synthesized by the conventional liquid or solid phase method. Furthermore, since the peptides of the present invention are basic peptides, they can be converted to appropriate acid-added salts according to conventional technique. Such preferred acid-added salts may be obtained by reaction with a pharmaceutically acceptable acid, and said salts include, for example, lactates, acetates, succinates, maleates, fumarates, tartarates, citrates, gluconates, ascorbates, benzoates, methanesulfonates, cinnamates, benzenesulfonates or phosphates, hydrogenphosphates, hydrochlorides, hydrobromides, hydroiodides, sulfamates, sulfates, trifluoroacetates, and the like.

The biological activity of the present peptides can be assayed according to the methods described in Japanese Patent Laid-Open No. 4-198161, in which excitatory postsynaptic potential (EPSP) is generated in the neuromuscular specimen of a lobster's walking leg, and the effect of the compound given to the nerve fibers on the EPSP is determined.

In general, substances inhibiting EPSP are believed to be glutamate antagonists or inhibitors for the release of glutamic acid, and the substances enhancing EPSP are believed to be glutamate-like agonists or accelerators for the release of glutamic acid.

As described in the Examples below, the peptides of the present invention show a remarkable effect of enhancing EPSP determined by the above assay. Accordingly, the compounds of the present invention are useful for enhancing cerebral neural activities and recovering muscular strength in the treatment of neuromuscular diseases. They are also useful as a tool for the study of neuroscience toward the elucidation of the transmission mechanism.

The present invention is now illustrated in more detail by way of the following examples, but it is to be noted that the present invention is not limited by these Examples in any way.

EXAMPLE 1

Isolation and Structure Determination of Peptides (1) and (97)

1) Isolation of Peptide (1)

The venom sacs of 60 female *Anoplius samariensis* were excised and lyophilized. These were homogenized in 1 ml of 50% acetonitrile/water containing 0.1% TFA and then centrifuged to obtain an extract. The precipitate was centrifuged again with 1 ml of 50% acetonitrile/water containing 0.1% TFA. This procedure was then repeated four times. All the extracts resulting from the above procedure carried out five times in total were collected and then evaporated under reduced pressure to obtain a crude extract.

The resulting crude extract was dissolved in water and then subjected to reversed phase HPLC (Waters Associates) using CAPCELL PAK C$_{18}$ φ 10 mm×250 mm (Shiseido Co., Ltd.,) with linear gradient from 5% to 95% acetonitrile/water containing 0.1% TFA at a flow rate of 2.5 ml/min over 30 minutes at room temperature. The peak fraction at a retention time of 19 min was collected by monitoring UV absorbance at 215 nm.

The obtained peak fraction was further subjected to HPLC using CAPCELL PAK C$_{18}$ φ 6 mm×150 mm (Shiseido Co., Ltd.,) with isocratic 29% acetonitrile/water containing 0.1%

TFA at a flow rate of 1 ml/min at room temperature, and the peak fraction at a retention time of 15 min was collected by monitoring UV absorbance at 215 nm. This fraction showed a single peak at a retention time of 11 min in HPLC using the above column (isocratic 30% acetonitrile/water containing 0.1% TFA).

The resulting fraction was lyophilized to yield 0.1 mg of peptide (1) as a trifluoroacetate.

2) Isolation of Peptide (97)

The venom sacs of 29 female *Batozonellus maculifrons* were excised and lyophilized. These were homogenized in 0.5 ml of 50% acetonitrile/water containing 0.1% TFA and then centrifuged to obtain an extract. The precipitate was centrifuged again with 0.5 ml of 50% acetonitrile/water containing 0.1% TFA. This procedure was then repeated four times. All the extracts resulting from the above procedure carried out five times in total were collected and then evaporated under reduced pressure to obtain a crude extract.

The resulting crude extract was dissolved in water and then subjected to reversed phase HPLC using CAPCELL PAK $C_{18}$ φ 10 mm×250 mm with linear gradient from 5% to 95% acetonitrile/water containing 0.1% TFA at a flow rate of 2.5 ml/min over 30 minutes at room temperature. The peak fraction at a retention time of 19 min was collected by monitoring UV absorbance at 215 nm.

The obtained peak fraction was further subjected to HPLC using CAPCELL PAK $C_{18}$ φ 6 mm×150 mm with isocratic 29% acetonitrile/water containing 0.1% TFA at a flow rate of 1 ml/min at room temperature, and the peak fractions at a retention time of 15 min and 16 min were collected by monitoring UV absorbance at 215 nm. The fraction obtained at a retention time of 15 min was lyophilized to yield 50 μg of peptide (1) as a trifluoroacetate and the fraction obtained at a retention time of 16 min was lyophilized to yield 30 μg of peptide (97) as a trifluoroacetate.

3) Determination of the Amino Acid Sequence

The amino acid sequences of the resulting peptides were determined by mass spectroscopy and Edman degradation. Mass spectroscopy was conducted by the Ladder sequencing method using carboxypeptidase and aminopeptidase and by MALDI-TOF-MS combined with the CID method. Distinction of Leu from Ile and Lys from Gln was demonstrated by the automatic Edman degradation using ABI 477A/120A Protein Sequencer (Applied Biosystems).

Furthermore, since a peak of m/z=1530 $(M+H)^+$ was observed in MALDI-TOF-MS, peptide (1) was found to have a sequence represented by SEQ ID NO: 1 in which the N-terminal is free and the C-terminal is amidated.

On the other hand, peptide (97) was identified with a sequence represented by SEQ ID NO: 2 by observing a peak of m/z=1558 $(M+H)^+$ in MALDI-TOF-MS.

EXAMPLE 2

Synthesis of Peptides (1) and (97)

Peptides (1) and (97) were synthesized using TGS-RAM-Resin (Shimadzu Corporation) as a carrier and Fmoc-amino acids in the solid phase method using the automatic peptide synthesizer PSSM-8 (Shimadzu Corporation).

Each of the synthesized peptides was then cleaved from the peptide resin and deprotected by adding a TFA solution containing 5% phenol, 5% thioanisole, 5% water, 3% 1,2-ethanedithiol and 2% ethylmethyl disulfide in an amount of 10 ml per gram of the peptide resin and then treating it at room temperature for 8 hours. After the treatment, ether was added to the TFA solution to precipitate the peptides, and the precipitate was washed three times with ether to obtain crude peptides. The crude peptides were purified by C-18 reversed phase HPLC. The resulting synthetic peptides (1) and (97) showed the same retention time in HPLC, the same mass spectra, and the same biological activity as the natural peptides (1) and (97), respectively.

EXAMPLE 3

Measurement of the Effect on Excitatory Postsynaptic Potential (EPSP)

The effect of the present peptides on excitatory postsynaptic potential (EPSP) was measured according to the method disclosed in Japanese Patent Laid-Open No. 4-198161. Thus, the shell of a lobster's walking leg was removed to expose the excitatory nerve and the inhibitory nerve, and a stimulating electrode was attached thereto. Then the nerve-muscle junction was exposed, and a recording electrode was attached thereto. The walking leg equipped with the electrodes was transferred to a container filled with an artificial seawater, and a partition was set up between the stimulating electrode part and the recording electrode part. The samples to be measured were dissolved into the artificial seawater in the recording electrode side (i.e., the side containing the nerve-muscle junction). Subsequently, the excitatory nerve was electrically stimulated and the EPSP, which was induced by glutamic acid released from the nerve end in response to the stimulation, was recorded.

When the effects of peptides (1) and (97) on EPSP were studied according to this method, peptide (1) enhanced EPSP at a concentration of $1 \times 10^{-6}$ M, and peptide (97) did at $2 \times 10^{-7}$ M.

INDUSTRIAL APPLICABILITY

The peptides provided by the present invention can be used as useful reagents to study the structure-activity relationship of their activities on the glutamate receptor in the field of neuroscience. Furthermore, they can be used as standard compounds in the study of neuroscience, especially in the study of neuropathic diseases such as Huntington's disease, epilepsy, Parkinson's disease and senile dementia, paving the way for pharmaceutical application of substances that act on the glutamate receptor.

What is claimed is:

1. An isolated peptide represented by the following amino acid sequence (SEQ ID NO:201):

H-X$_1$-X$_2$-X$_3$-X$_4$-Gly-X$_6$-X$_7$-Asp-Gln-R wherein:
each of X$_1$ and X$_3$ independently represents Arg or Lys, each of X$_2$, X$_4$
and X$_6$ independently represents Ile or Leu, and X$_7$ represents Phe, Tyr or Trp; and
R represents -Leu-Ser-Lys-Leu-NH$_2$ or -Leu-Ser-Arg-Leu-NH$_2$; and a salt thereof.

2. The isolated peptide as claimed in claim 1 represented by the following amino acid sequence (SEQ ID NO:7):

H-X$_1$-X$_2$-X$_3$-X$_4$-Gly-X$_6$-X$_7$-Asp-Gln-Leu-Ser-Lys-Leu-NH$_2$ wherein:
each of X$_1$ and X$_3$ independently represents Arg or Lys, each of X$_2$, X$_4$ and
X$_6$ independently represents Ile or Leu, and X$_7$ represents Phe, Tyr or
Trp;
and a salt thereof.

3. The isolated peptide as claimed in claim 1 represented by the following amino acid sequence (SEQ ID NO:8):

H-X$_1$-X$_2$-X$_3$-X$_4$-Gly-X$_6$-X$_7$-Asp-Gln-Leu-Ser-Arg-Leu-NH$_2$ wherein:
each of X$_1$ and X$_3$ independently represents Arg or Lys, each of X$_2$, X$_4$ and
X$_6$ independently represents Ile or Leu, and X$_7$ represents Phe, Tyr or
Trp;
and a salt thereof.

4. The isolated peptide as claimed in claim 1 represented by the following amino acid sequence (SEQ ID NO:202):

H-Arg-Ile-Lys-Ile-Gly-Leu-Phe-Asp-Gln-Leu-Ser-Lys-Leu-NH$_2$ and a salt thereof.

5. The isolated peptide as claimed in claim 1 represented by the following amino acid sequence (SEQ ID NO:203):

H-Arg-Ile-Lys-Ile-Gly-Leu-Phe-Asp-Gln-Leu-Ser-Arg-Leu-NH$_2$ and a salt thereof.

6. The isolated peptide and a salt as claimed in claim 1 as a glutamate receptor agonist.

* * * * *